United States Patent
Sugimoto

(10) Patent No.: US 8,226,551 B2
(45) Date of Patent: Jul. 24, 2012

(54) SCANNING ENDOSCOPE, SCANNING ENDOSCOPE PROCESSOR, AND SCANNING ENDOSCOPE APPARATUS

(75) Inventor: Hideo Sugimoto, Tokyo (JP)

(73) Assignee: Hoya Corporation, Tokyo (JP)

( * ) Notice: Subject to any disclaimer, the term of this patent is extended or adjusted under 35 U.S.C. 154(b) by 442 days.

(21) Appl. No.: 12/619,934

(22) Filed: Nov. 17, 2009

(65) Prior Publication Data

US 2010/0125170 A1    May 20, 2010

(30) Foreign Application Priority Data

Nov. 19, 2008 (JP) ................................. 2008-296143

(51) Int. Cl.
    *A61B 1/06*      (2006.01)
(52) U.S. Cl. .................... 600/170; 600/173; 600/176
(58) Field of Classification Search .............. 600/160, 600/170–171, 173, 176, 182; 385/117
See application file for complete search history.

(56) References Cited

U.S. PATENT DOCUMENTS

| | | | | |
|---|---|---|---|---|
| 5,940,126 A | * | 8/1999 | Kimura | .......................... 600/173 |
| 6,294,775 B1 | | 9/2001 | Seibel et al. | |
| 7,129,472 B1 | | 10/2006 | Okawa et al. | |
| 7,218,822 B2 | * | 5/2007 | Treado et al. | ................. 385/117 |
| 7,349,098 B2 | * | 3/2008 | Li | .................................. 356/479 |
| 7,608,842 B2 | * | 10/2009 | Johnston | ........................ 385/117 |
| 7,616,986 B2 | | 11/2009 | Seibel et al. | |
| 7,833,152 B2 | * | 11/2010 | Chatenever et al. | .......... 600/173 |
| 2001/0055462 A1 | * | 12/2001 | Seibel | ............................ 385/147 |
| 2004/0254474 A1 | | 12/2004 | Seibel et al. | |
| 2007/0035797 A1 | | 2/2007 | Kanai | |
| 2007/0129601 A1 | * | 6/2007 | Johnston et al. | .............. 600/109 |

FOREIGN PATENT DOCUMENTS

| | | |
|---|---|---|
| JP | 2001-174744 | 6/2001 |
| JP | 3943927 | 4/2007 |
| JP | 2008-504557 | 2/2008 |
| WO | 2006/004743 | 1/2006 |

OTHER PUBLICATIONS

U.S. Appl. No. 12/619,915 to Sugimoto, filed Nov. 17, 2009.

* cited by examiner

*Primary Examiner* — Christopher Mahoney
(74) *Attorney, Agent, or Firm* — Greenblum & Bernstein, P.L.C.

(57) ABSTRACT

A scanning endoscope, comprising a first transmitter, an actuator, and a mirror, is provided. The first transmitter emits a beam of radiant light from the first emission end. The actuator moves the first emission end in a direction perpendicular to an emission direction. The mirror is arranged from the first emission end to the first direction. The mirror comprises a through-part and a reflection surface. The radiant light emitted from the first emission end passes through the through-part when the first emission end is within a first circumference. The reflection surface reflects the radiant light emitted from the first emission end toward the observation area around the first straight line when the first emission end is outside of the first circumference.

11 Claims, 21 Drawing Sheets

SCANNING ENDOSCOPE, SCANNING ENDOSCOPE PROCESSOR, AND SCANNING ENDOSCOPE APPARATUS

BACKGROUND OF THE INVENTION

1. Field of the Invention

The present invention relates to a scanning endoscope that photographs and/or films an optical image of a front view of a subject that is circumferentially located around an insertion tube of the scanning endoscope.

2. Description of the Related Art

Japanese Patent No. 3943927 discloses a scanning endoscope which photographs and/or films an optical image of an observation area by scanning the observation area with light shined on a minute point in the area and successively capturing reflected light at the illuminated points. In a general scanning endoscope, light for illumination is transmitted through an optical fiber from a stationary incident end to a movable emission end and a scanning operation is carried out by successively moving the emission end of the optical fiber.

A general scanning endoscope is designed so that a field of vision of the scanning endoscope is in front of a distal end of an insertion tube of the scanning endoscope. However, it is difficult to observe certain types of subjects using such scanning endoscope. This is because it is difficult to adjust the position of the insertion tube in a thin lumen, such as a bronchial periphery, so that the distal end of the insertion tube faces the inner surface of the thin lumen. Accordingly, the inner surface of a thin lumen is photographed and/or filmed at a large angle of incidence with respect to the inner surface to be photographed and/or filmed. However, it is difficult to recognize the status of the inner surface by the image of the inner surface photographed and/or filmed from a large angle of incidence.

SUMMARY OF THE INVENTION

Therefore, an object of the present invention is to provide a scanning endoscope that can photograph and/or film optical images, which are front views of subjects, in front of the distal end of an insertion tube and around the periphery surrounding the insertion tube.

According to the present invention, a scanning endoscope, comprising a first transmitter, an actuator, and a mirror, is provided. The first transmitter has a first emission end. The first transmitter emits a beam of radiant light from the first emission end. The beam of the radiant light is shined on an observation area. The actuator moves the first emission end in a direction perpendicular to an emission direction. The beam of the radiant light is emitted from the first emission end of the first transmitter in the emission direction. The mirror is arranged from the first emission end to the first direction. The first direction is the emission direction when the emission end is on a standard point. The mirror comprises a through-part and a reflection surface. The radiant light emitted from the first emission end passes through the through-part when the first emission end is within a first circumference. A center of the first circumference is in agreement with the standard point. The radius of the first circumference is a first length. The reflection surface is formed around a first straight line. The first straight line is parallel to the first direction and including the standard point. The distance between a first position on the first straight line and any second position on the reflection surface increases as the first position is moved in the first direction. The reflection surface reflects the radiant light emitted from the first emission end toward the observation area around the first straight line when the first emission end is outside of the first circumference. A line connecting the first and second positions is perpendicular to the first straight line.

According to the present invention, a scanning endoscope processor, comprising a light source, a light receiver, an image processor, and a controller, is provided. The light source supplies the radiant light that is emitted from the first emission end to the first transmitter of the scanning endoscope. The light receiver receives and detects the amount of reflected light or fluorescence at the observation area illuminated with the radiant light. The image processor produces an image corresponding to the observation area on the basis of the amount of the reflected light or the fluorescence detected by the light receiver. The controller orders the image processor to generate a front image when the first emission end is moved within the first circumference. The controller orders the image processor to generate a side image when the first emission end is moved outside of the first circumference. The front image is an image of the observation area in the first direction from the first emission end. The side image is an image of the observation area around the first straight line near the first emission end.

According to the present invention, a scanning endoscope apparatus, comprising the scanning endoscope and the scanning endoscope processor, is provided.

BRIEF DESCRIPTION OF THE DRAWINGS

The objects and advantages of the present invention will be better understood from the following description, with reference to the accompanying drawings in which.

DESCRIPTION OF THE PREFERRED EMBODIMENTS

Figure 1:
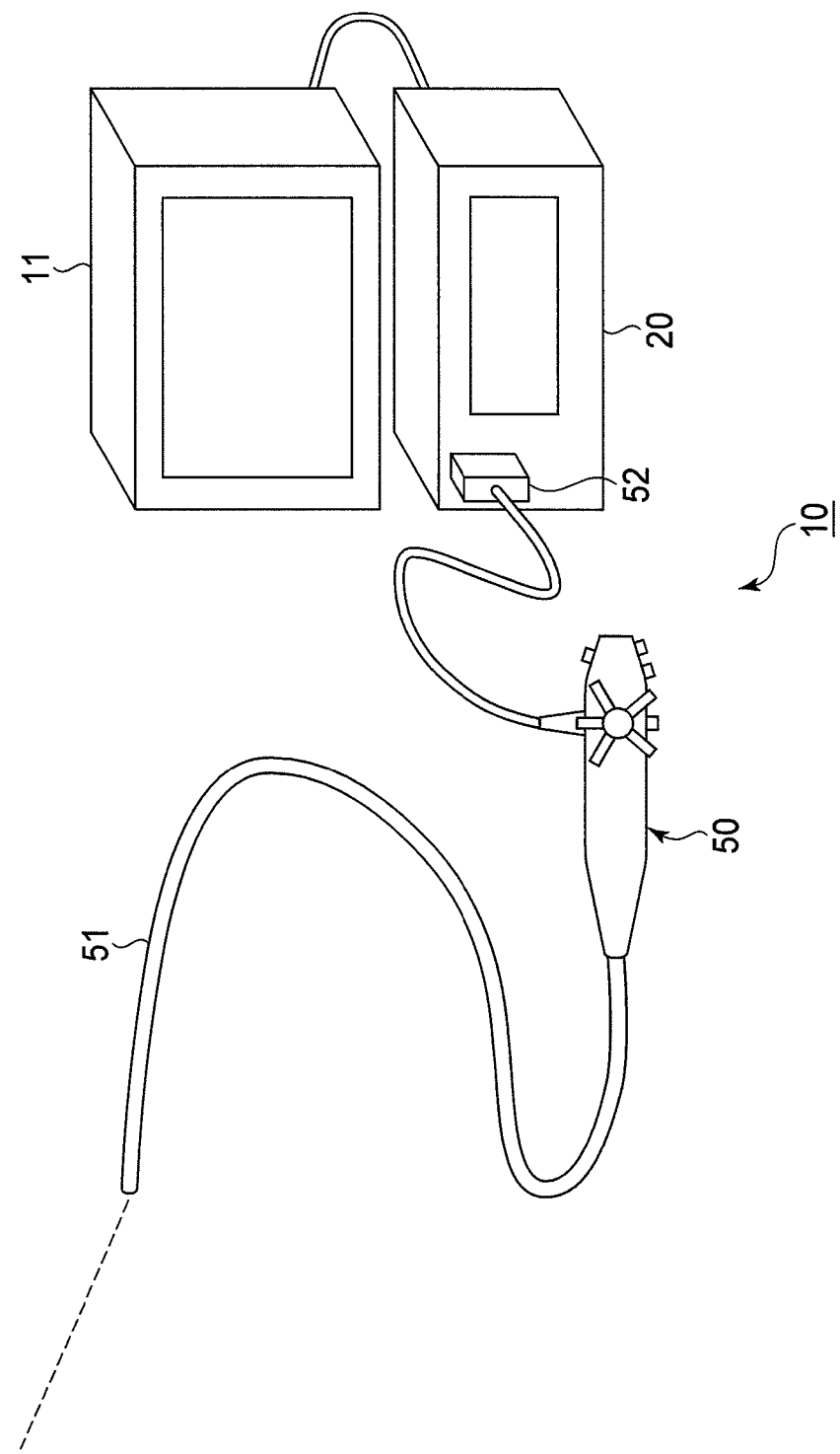
FIG. 1 is a schematic illustration of a scanning endoscope apparatus comprising a scanning endoscope and a scanning endoscope processor of the embodiment of the present invention.

The present invention is described below with reference to the embodiment shown in the drawings.

In FIG. 1, the scanning endoscope apparatus 10 comprises a scanning endoscope processor 20, a scanning endoscope 50, and a monitor 11. The scanning endoscope processor 20 is connected to the scanning endoscope 50 and the monitor 11.

Hereinafter, an emission end of an illumination fiber (not depicted in FIG. 1) and incident ends of first and second image fibers (not depicted in FIG. 1) are ends mounted in the distal end of the insertion tube 51 of the scanning endoscope 50. In addition, an incident end of the illumination fiber and emission ends of the first and second image fibers are ends mounted in a connector 52, with which the scanning endoscope processor 20 is connected.

The scanning endoscope processor 20 provides light that is shined on first and second observation areas, which are described later. The light emitted from the scanning endoscope processor 20 is transmitted to the distal end of the insertion tube 51 through the illumination fiber (first transmitter), and is shined towards two points in the first and second observation areas. Light reflected from the illuminated point is transmitted from the distal end of the insertion tube 51 to the scanning endoscope processor 20.

The direction of the emission end of the illumination fiber is changed by a fiber actuator (not depicted in FIG. 1). By changing the direction, the first and second observation areas are scanned with the light emitted from the illumination fiber. The fiber actuator is controlled by the scanning endoscope processor 20.

The scanning endoscope processor 20 receives reflected light which is scattered at the illuminated point, and generates a pixel signal according to the amount of received light. One frame of an image signal is generated by generating pixel signals corresponding to the illuminated points entirely dispersed in the observation area. The generated image signal is transmitted to the monitor 11, where an image corresponding to the received image signal is displayed.

Figure 2:
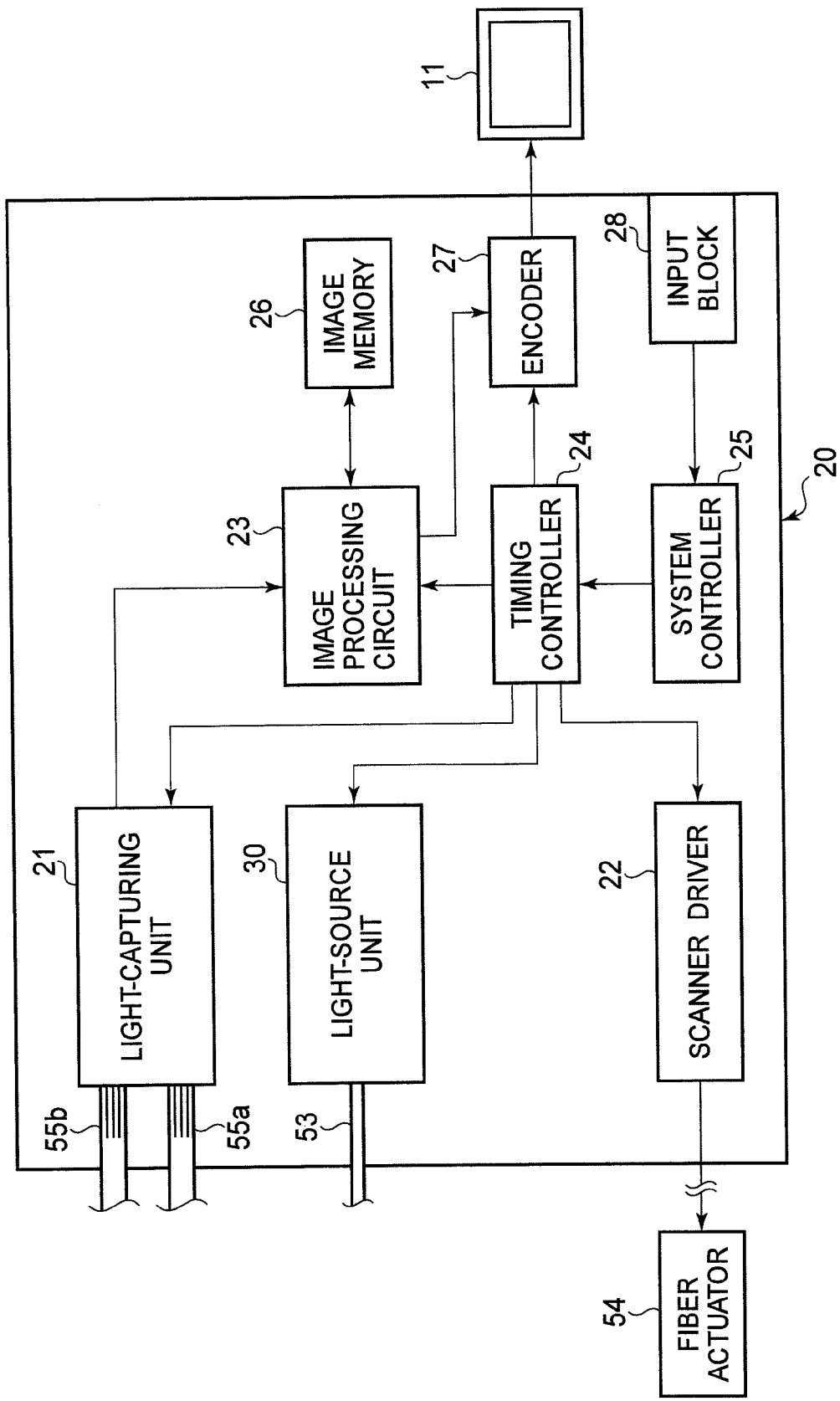
FIG. 2 is a block diagram schematically showing the internal structure of the scanning endoscope processor.

As shown in FIG. 2, the scanning endoscope processor 20 comprises a light-source unit 30, a light-capturing unit 21, a scanner driver 22, an image processing circuit 23, a timing controller 24, a system controller 25, and other components.

The light-source unit 30 comprises red, green, and blue lasers (not depicted), which emits red, green, and blue laser beams, respectively. The red, green, and blue laser beams are mixed into white laser beam, which is emitted from the light-source unit 30.

The light-source unit 30 provides the illumination fiber 53 with white laser beam that is emitted from the light-source unit 30. The scanning driver 22 controls the fiber actuator 54 to move the emission end of the illumination fiber 53 along a predetermined course.

The reflected light at the first and second observation areas is transmitted to the scanning endoscope processor 20 by the first and second image fibers 55a and 55b that the scanning endoscope 50 comprises. The transmitted light is made incident on the light-capturing unit 21.

The light-capturing unit 21 generates a pixel signal according the amount of the reflected light. The pixel signal is transmitted to the image processing circuit 23, which stores the received pixel signal in the image memory 26. Once pixel signals corresponding to the illuminated points dispersed throughout the first and second observation areas have been stored, the image processing circuit 23 carries out predetermined image processing on the pixel signals, and then one frame of the image signal is transmitted to the monitor 11 via the encoder 27.

By connecting the scanning endoscope 50 to the scanning endoscope processor 20, optical connections are made; between the light-source unit 30 and the illumination fiber 53 mounted in the scanning endoscope 50, and between the light-capturing unit 21 and the first and second image fibers 55a and 55b. In addition, by connecting the scanning endoscope 50 to the scanning endoscope processor 20, the fiber actuator 54 mounted in the scanning endoscope 50 is electrically connected with the scanning driver 22.

The timing for carrying out operations of the light-source unit 30, the light-capturing unit 21, the image processing circuit 23, the scanning driver 22, and the encoder 27 is controlled by the timing controller 24. In addition, the timing controller 24 and other components of the endoscope apparatus 10 are controlled by the system controller 25. A user can input some commands to the input block 28, which comprises a front panel (not depicted) and other mechanisms.

Figure 3:
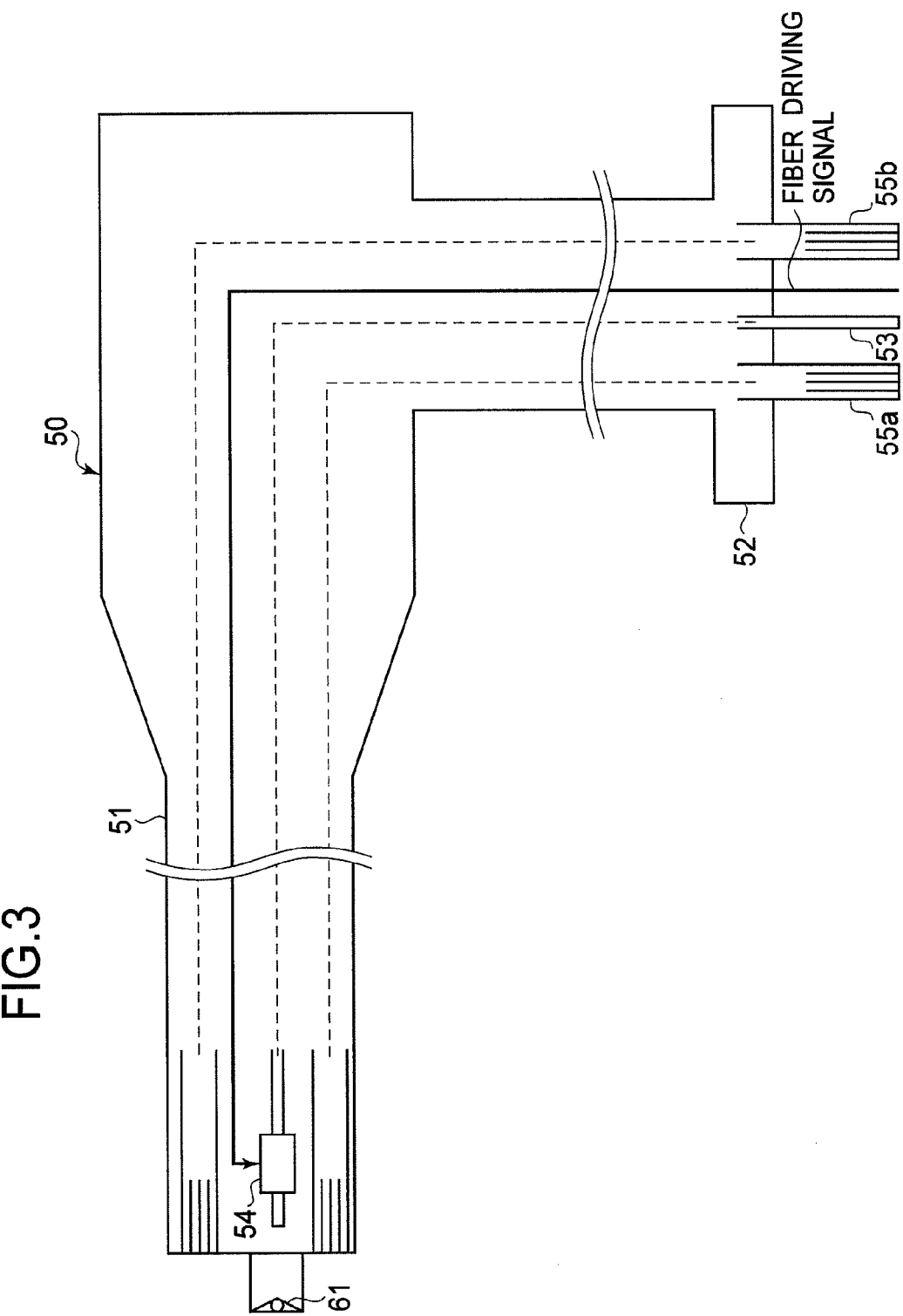
FIG. 3 is a block diagram schematically showing the internal structure of the scanning endoscope.

Next, the structure of the scanning endoscope 50 is explained. As shown in FIG. 3, the scanning endoscope 50 comprises the illumination fiber 53, the fiber actuator 54, the first and second image fibers 55a and 55b, a mirror 61, and other components.

The illumination fiber 53 and the first and second image fibers 55a and 55b are arranged inside the scanning endoscope 50 from the connector 52 to the distal end of the insertion tube 51. As described above, the white laser beam emitted by the light-source unit 30 is incident on the incident end of the illumination fiber 53. The incident white laser beam is transmitted to the emission end of the illumination fiber 53.

Figure 4:
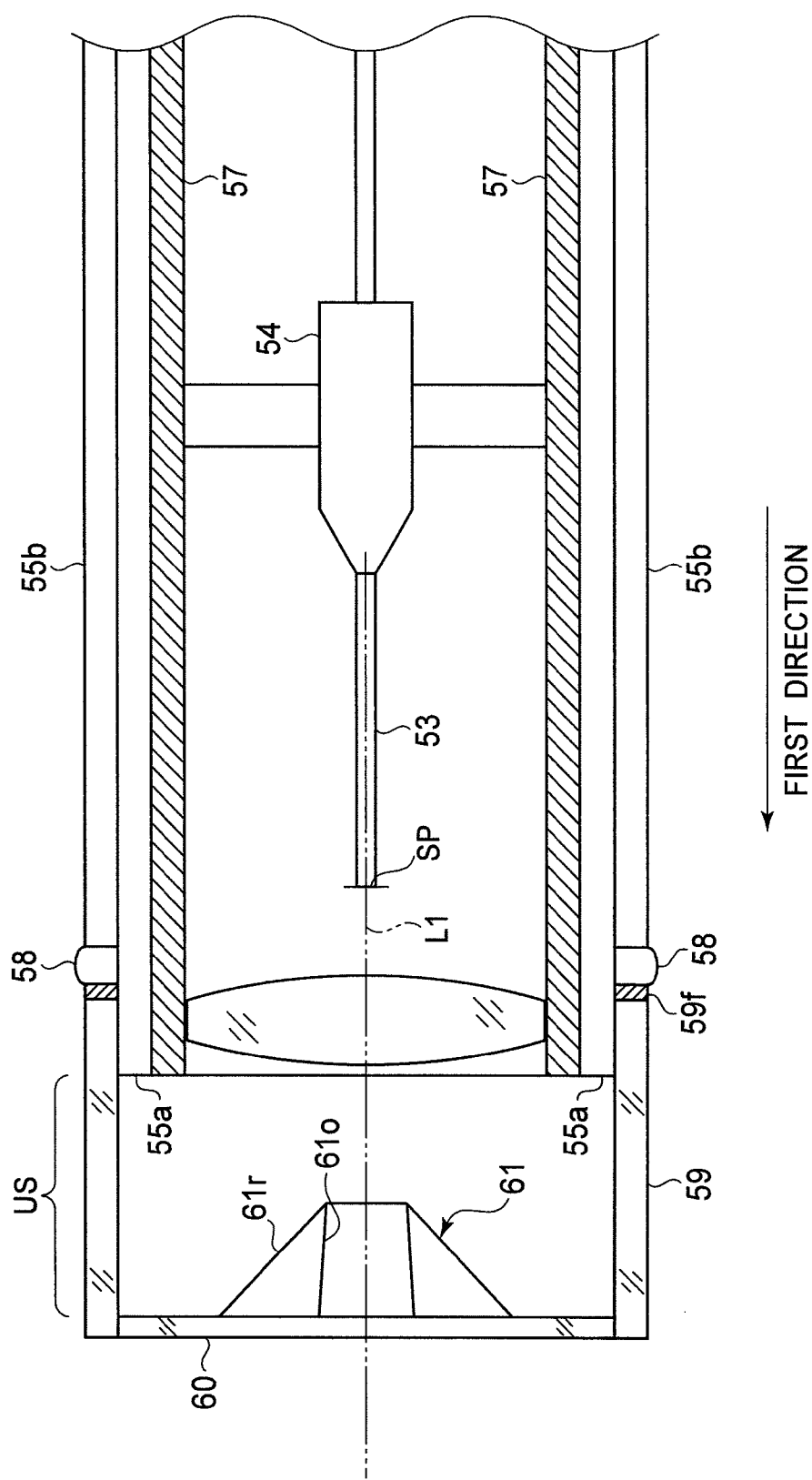
FIG. 4 is a sectional view of the emission end of the illumination fiber along the axis direction of the illumination fiber.

As shown in FIG. 4, a solid hollow tube 57 is mounted at the distal end of the insertion tube 51. The hollow tube 57 is positioned so that the axis directions of the distal end of the insertion tube 51 and the hollow tube 57 are parallel.

The illumination fiber 53 is supported inside the hollow tube 57 by the fiber actuator 54. The illumination fiber 53 is positioned in the hollow tube 57 so that the axis direction of the hollow tube 57 is parallel to a first direction, which is an axis direction of the insertion tube 51 that is not moved by the fiber actuator 54.

Figure 5:
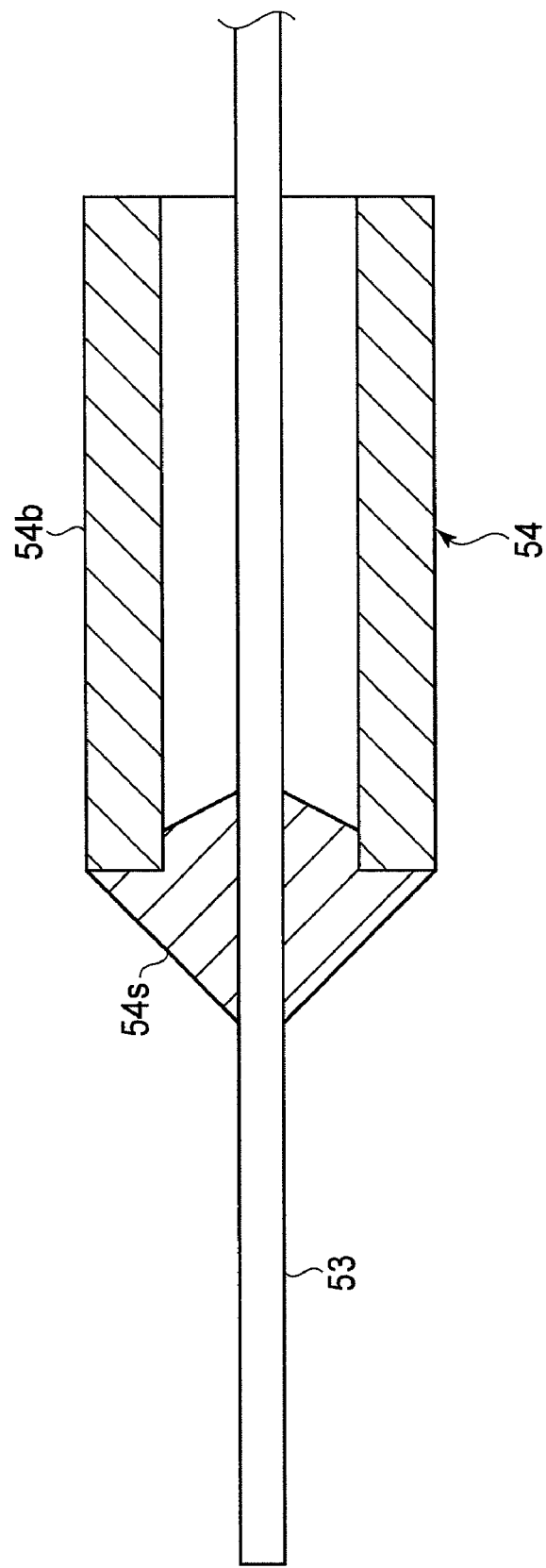
FIG. 5 is a sectional view of the fiber actuator along the axis direction of the illumination fiber for the purpose of illustrating the structure of the fiber actuator.

As shown in FIG. 5, the fiber actuator 54 comprises a supporting block 54s and a bending block 54b. The bending block 54b is shaped cylindrically. The illumination fiber 53 is inserted through the cylindrical bending block 54b. The illumination fiber 53 is supported at the forward end of the bending block 54b nearest the distal end of the insertion tube 51 by the supporting block 54s.

Figure 6:
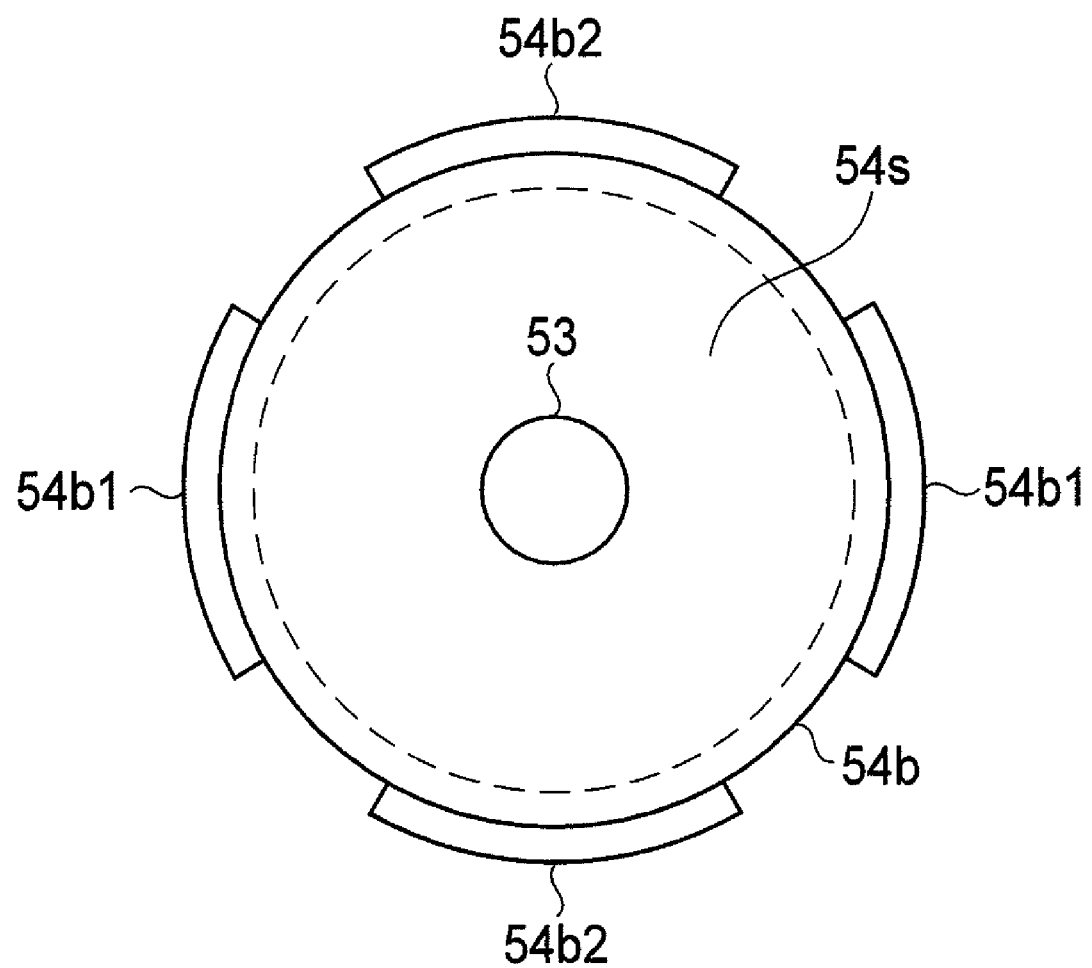
FIG. 6 is a front view of the fiber actuator as seen from the emission end of the illumination fiber.

As shown in FIG. 6, first and second bending elements 54b1 and 54b2 are fixed on the bending block 54b. The first and second bending elements 54b1 and 54b2 are pairs of two piezoelectric elements. In addition, the first and second bending elements 54b1 and 54b2 expand and contract along the axis direction of the cylindrical bending block 54b on the basis of a fiber driving signal transmitted from the scanner driver 22.

Two piezoelectric elements that constitute the first bending element 54b1 are fixed on the outside surface of the cylindrical bending block 54b so that the axis of the cylindrical bending block 54b is between the piezoelectric elements. In addition, two piezoelectric elements that constitute the second bending element 54b2 are fixed on the outside surface of the cylindrical bending block 54b at a location that is 90 degrees circumferentially from the first bending element 54b1 around the axis of the cylindrical bending block 54b.

Figure 7:
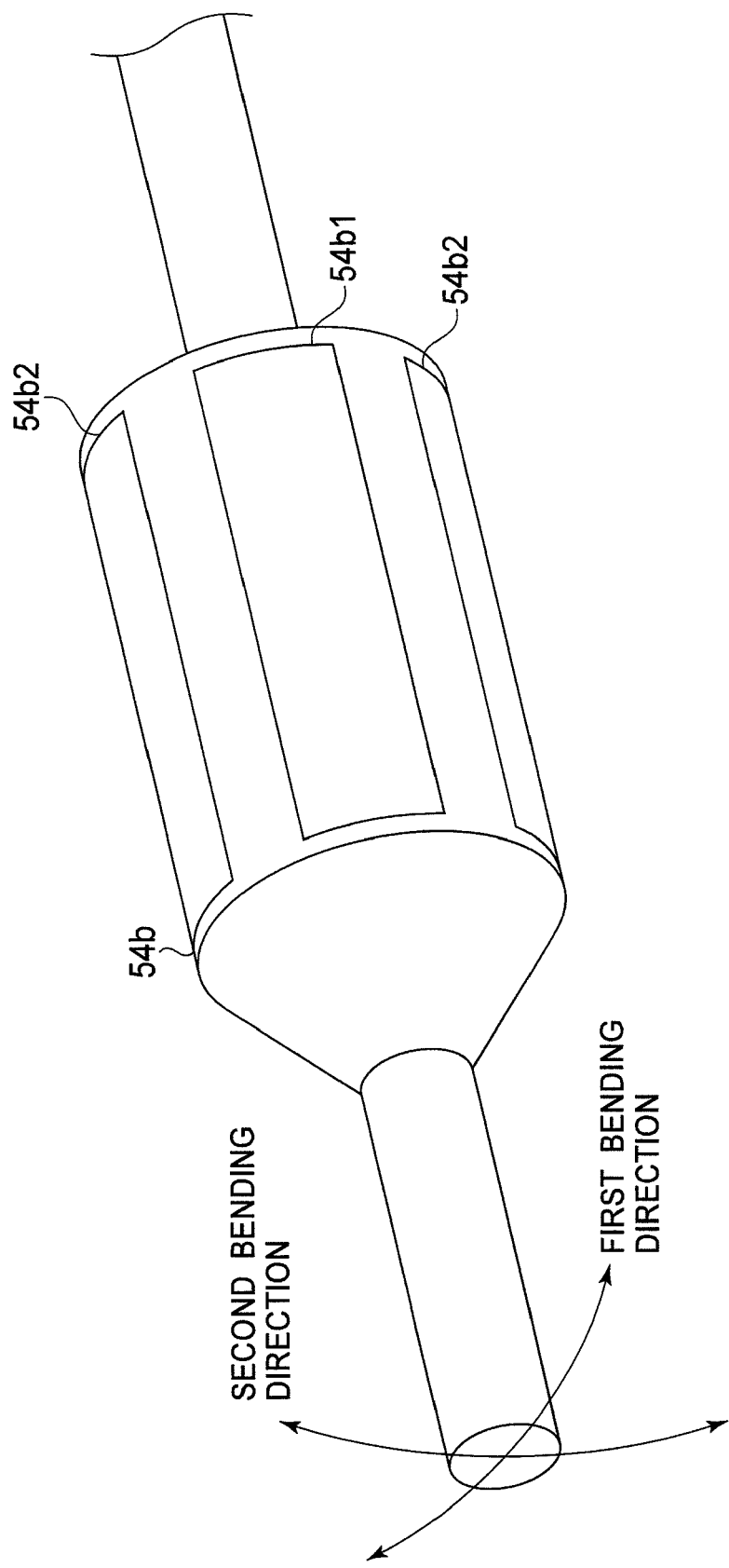
FIG. 7 is a perspective view of the fiber actuator.

As shown in FIG. 7, the bending block 54b bends along a first bending direction by expanding one of the piezoelectric elements that constitute the first bending element 54b1 and contracting the other at the same time. The piezoelectric elements constituting the first bending element 54b1 are arranged along the first bending direction, t.

In addition, the bending block 54b bends along a second bending direction by expanding one of the piezoelectric elements that constitute the second bending element 54b2 and contracting the other at the same time. The piezoelectric elements constituting the second bending element 54b2 are arranged along the second bending direction.

The side of illumination fiber 53 is pushed along the first and/or second bending directions by the bending block 54b via the supporting block 54s, and the illumination fiber 53 bends toward the first and/or second bending directions, which are perpendicular to the axis direction of the illumination fiber 53. The emission end of the illumination fiber 53 is moved by bending the illumination fiber 53.

Figure 8:
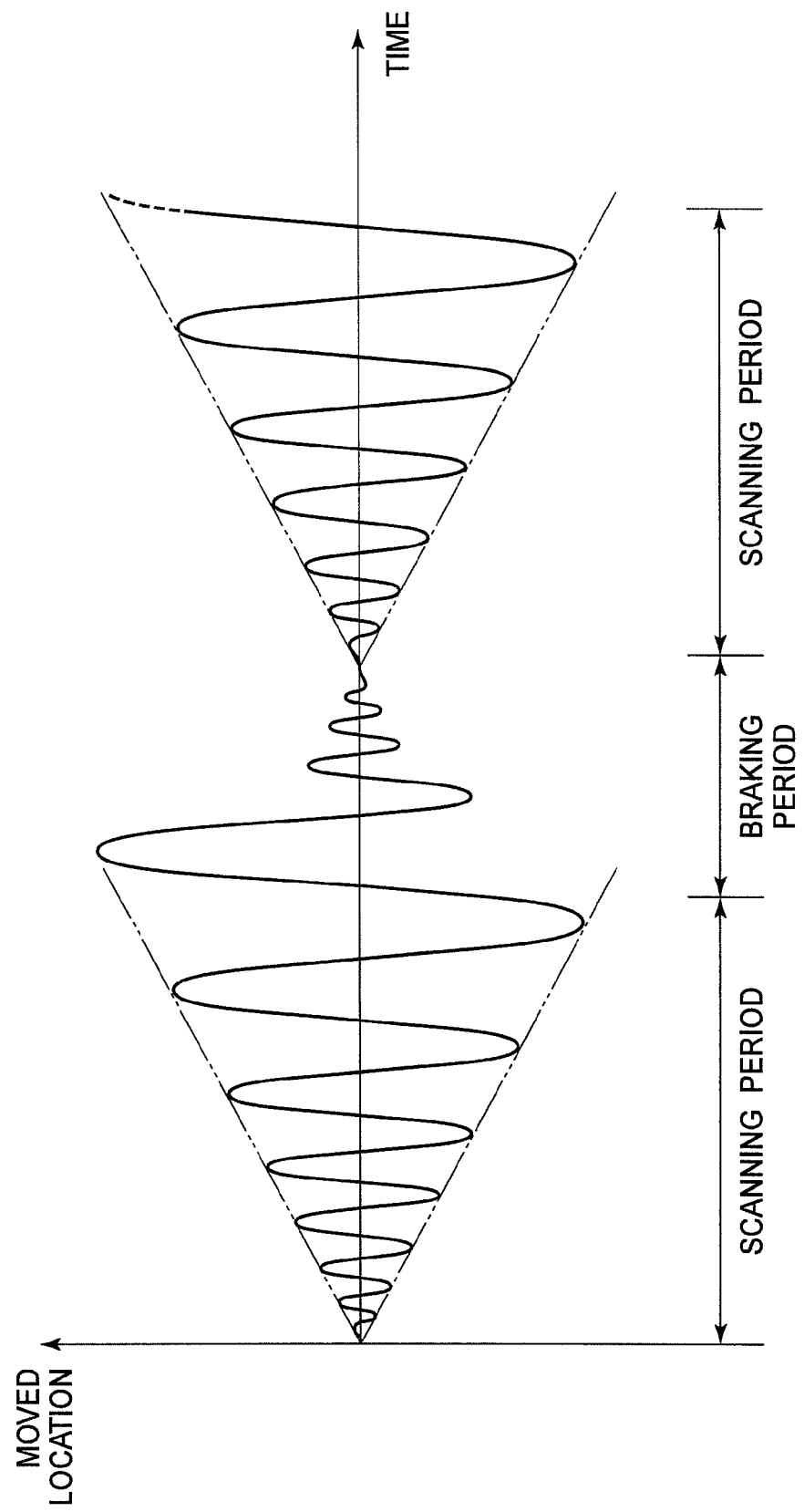
FIG. 8 is a graph illustrating the change in position of the emission end from the standard point along the first and second bending directions.

As shown in FIG. 8, the emission end of the illumination fiber 53 is moved so that the emission end vibrates along the first and second bending directions at amplitudes that are repetitively increased and decreased. The frequencies of the vibration along the first and second bending directions are adjusted to be equal. In addition, the period to increase and to decrease the amplitudes of the vibration along the first and second bending directions are synchronized. Further, phases of the vibration along the first and second bending directions are shifted by 90 degrees.

Figure 9:
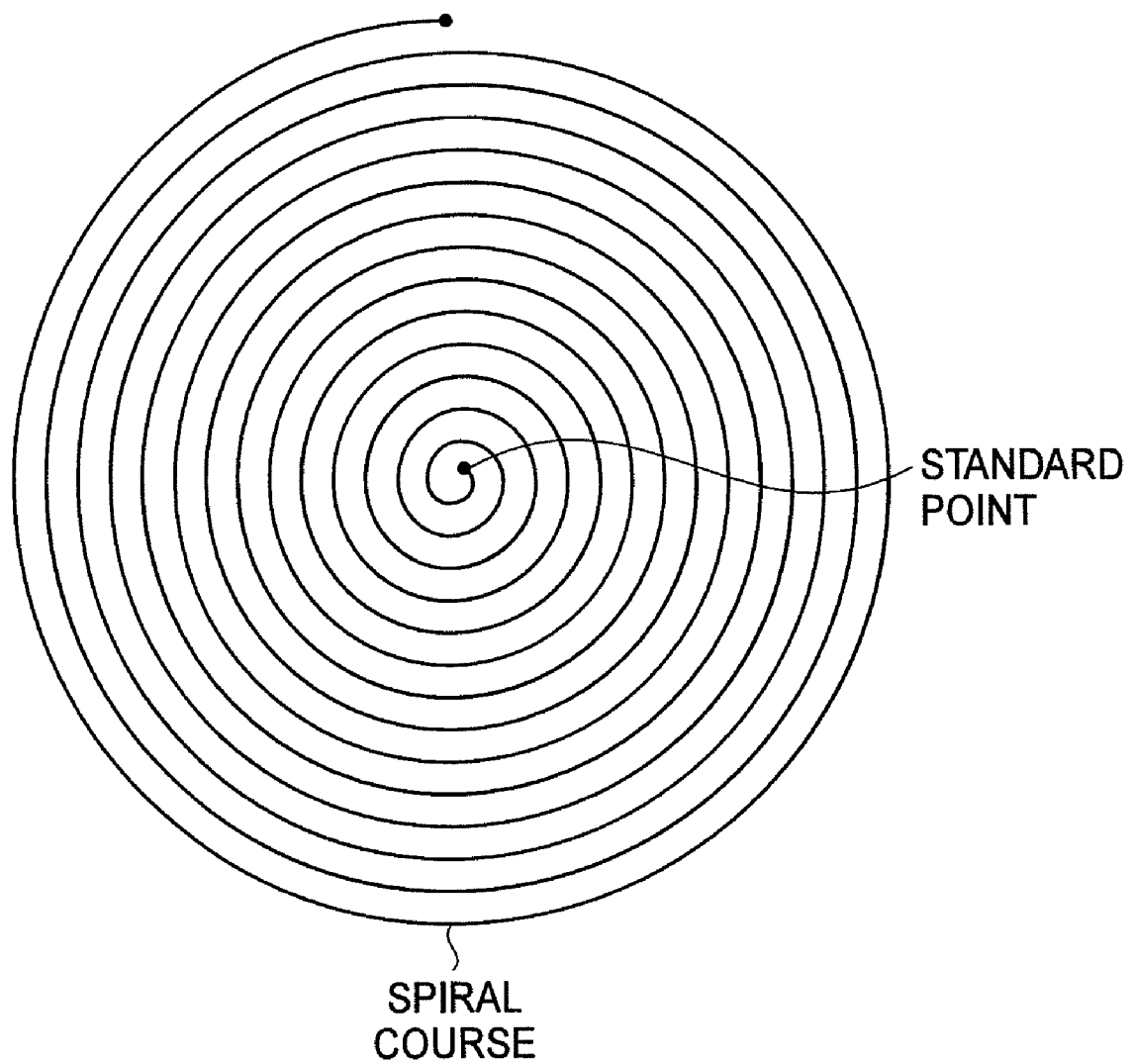
FIG. 9 is an illustration of a spiral course along which the emission end of the illumination fiber is moved by the fiber actuator.

By vibrating the emission end of the illumination fiber 53 along the first and second bending directions as described above, the emission end traces the spiral course shown in FIG. 9, and the first and second observation areas are scanned with the white laser beam.

The position of the emission end of the illumination fiber 53 when it is not bent is defined as a standard point (see FIGS. 4 and 9). As described later, while the emission end is vibrated with increasing the amplitude starting from the standard point (see "scanning period" in FIG. 8), illumination of the first and second observation areas with the white laser beam and generation of pixel signals are carried out.

In addition, when the amplitude reaches a maximum among the predetermined range, one scanning operation for producing one image terminates. After termination of a scanning operation, the emission end of the illumination fiber 53 is returned on the standard point by vibration of the emission end along the first and second bending directions at decreasing amplitudes during a braking period, as shown in FIG. 8. When the emission end is moved to the standard point, it is the beginning of a scanning operation for generating another image.

Figure 10:
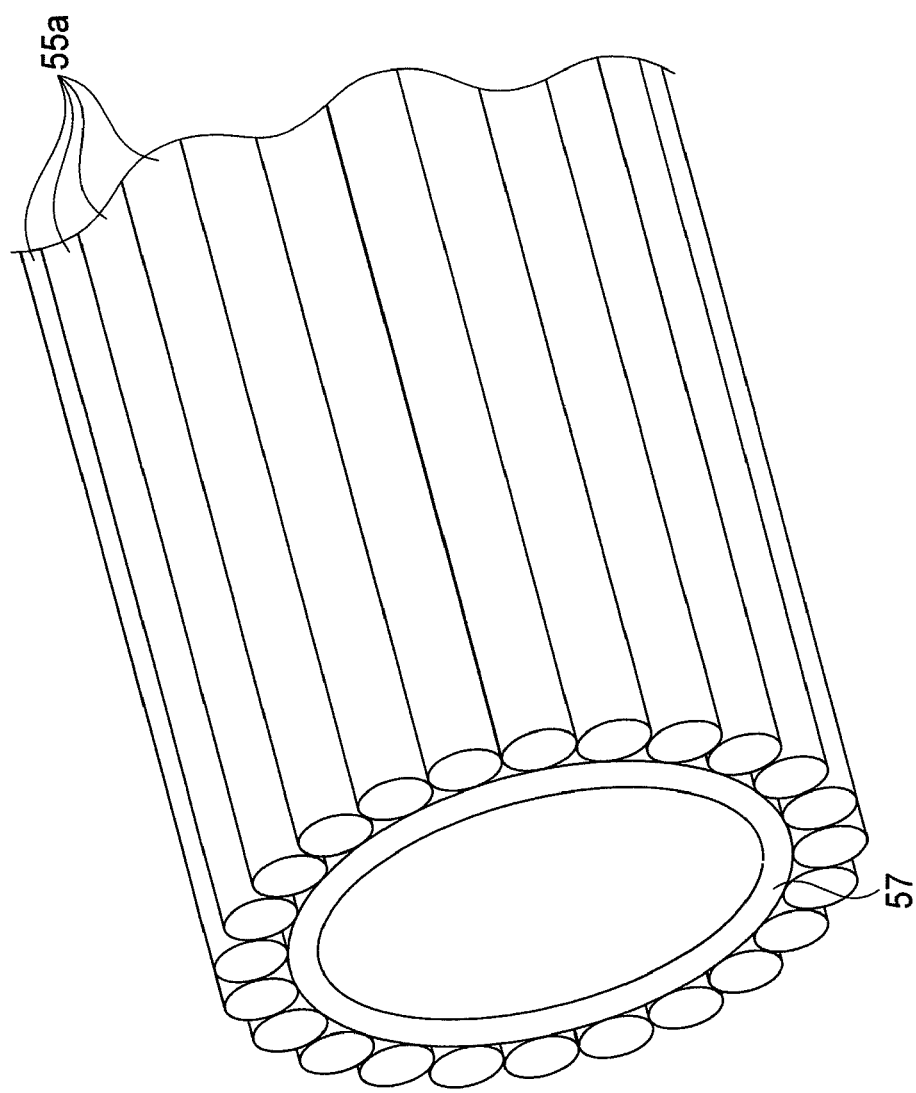
FIG. 10 is a perspective view of the first image fibers and the hollow tube for the purpose of illustrating the arrangement of the first image fibers on the hollow tube.

As shown in FIGS. 4 and 10, a plurality of the first image fibers 55a are fixed around the hollow tube 57 so that the first image fibers 55a surround the hollow tube 57. In addition, the first image fibers 55a are fixed so that the axis directions of the first image fibers 55a at the incident end and the hollow tube 57 are parallel. In addition, the first image fibers 55a are fixed so that the incident ends of the first image fibers 55a and the end of the hollow tube 57 toward the distal end of the insertion tube 51 are all evenly aligned.

Figure 11:
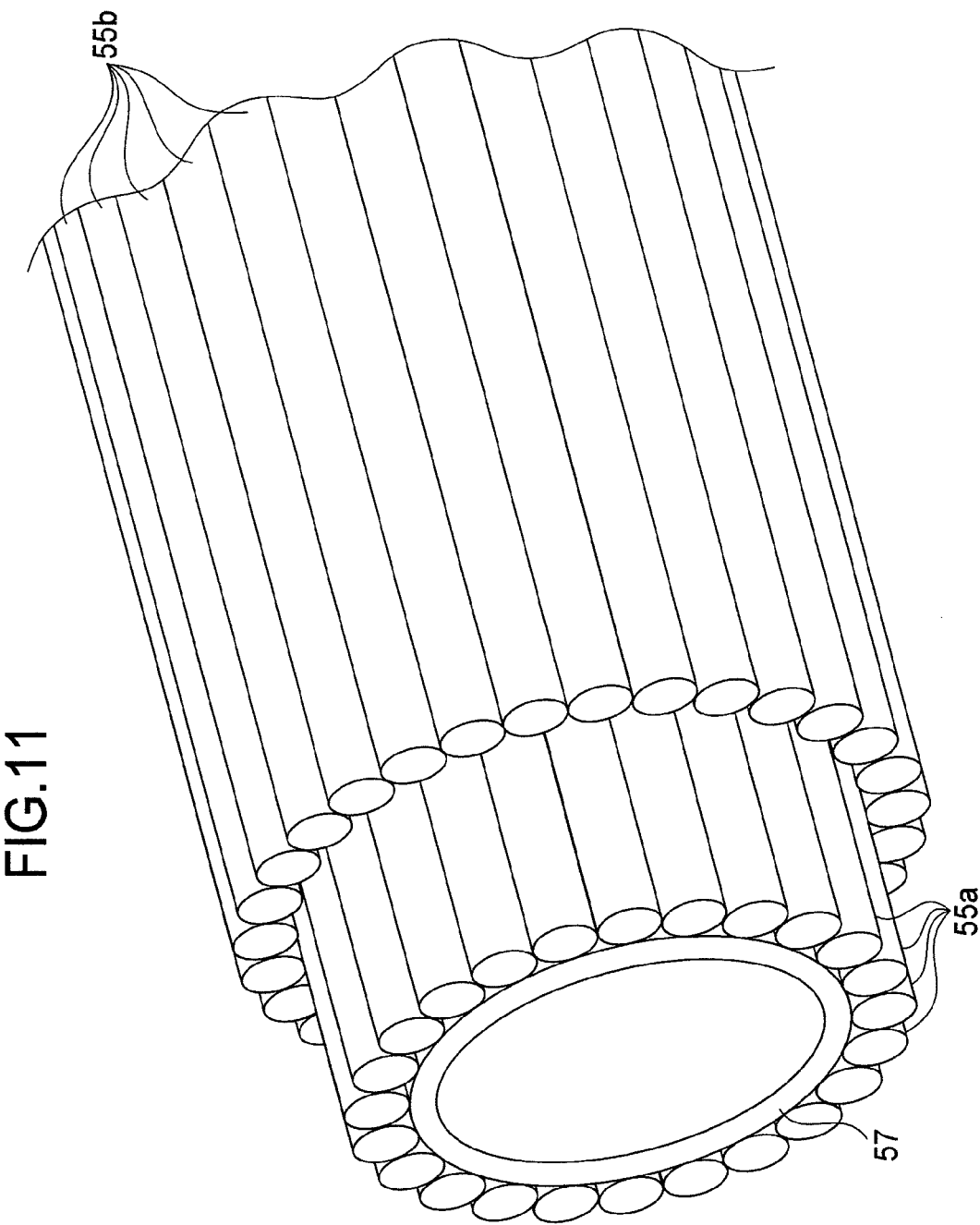
FIG. 11 is a perspective view of the first and second image fibers and the hollow tube for the purpose of illustrating the arrangement of the first and second image fibers on the hollow tube.

As shown in FIGS. 4 and 11, a plurality of the second image fibers 55b is fixed around the hollow tube 57, which is surrounded by the first image fibers 55a, so that the second image fibers 55b surround the bundle of the first image fibers 55a on the hollow tube 57. In addition, the second image fibers 55b are fixed so that the axis directions of the second image fibers 55b are parallel to the hollow tube 57 at the incident end. In addition, the second image fibers 55b are fixed so that the incident ends of the first image fibers 55a protrude from the incident ends of the second image fibers 55b.

Figure 12:
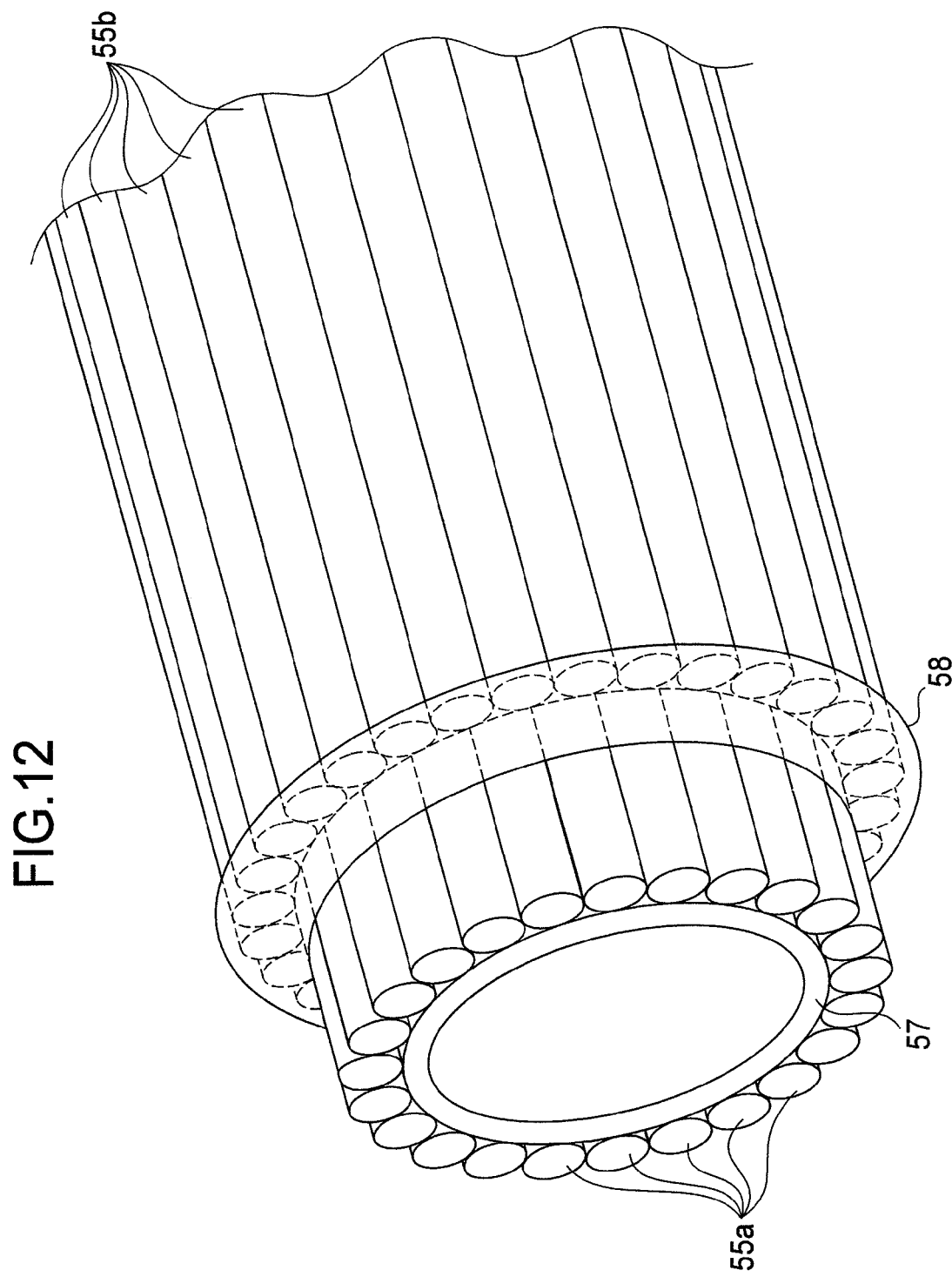
FIG. 12 is a perspective view of the first and second image fibers, the hollow tube, and the ring lens for the purpose of illustrating the arrangement of the first and second image fibers and the ring lens on the hollow tube.

As shown in FIGS. 4 and 12, the hollow tube 57 and the bundle of the first image fibers 55a are inserted inside a ring lens 58. The ring lens 58 is adhered to the incident ends of the second image fibers 55b.

Figure 13:
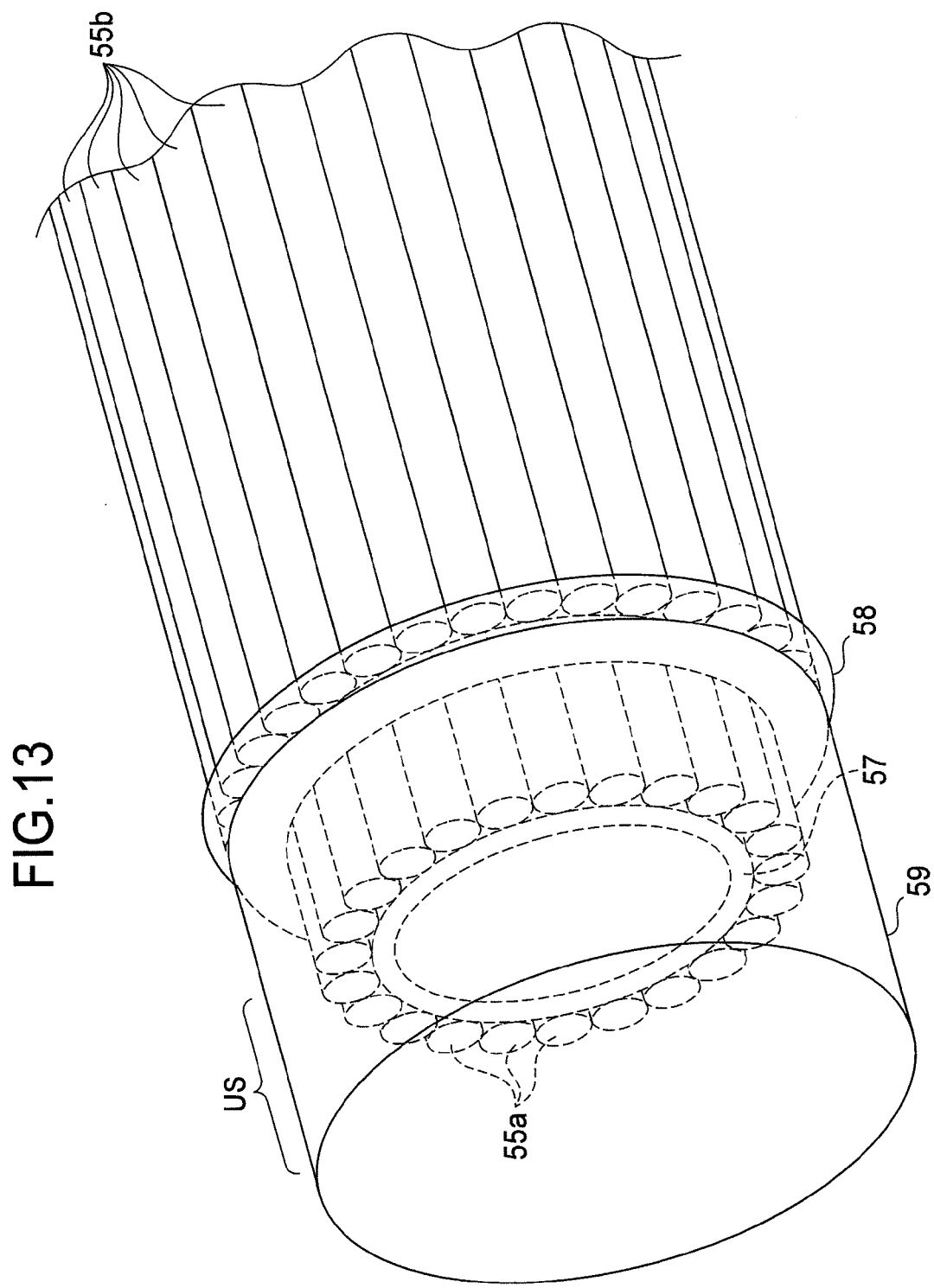
FIG. 13 is a perspective view of the first and second image fibers, the hollow tube, the ring lens, and the tubular glass for the purpose of illustrating the arrangement of the first and second image fibers, the ring lens, and the tubular glass on the hollow tube.

In addition, as shown in FIGS. 4 and 13, a head end of the hollow tube 57 and the bundle of the first image fibers 55a are attached together and inserted inside the tubular glass 59. The hollow tube 57 and the bundle of the first image fibers 55a are also fixed together, but the distal end of the hollow tube 57 and the bundle of the first image fibers 55a do not pierce the tubular glass 59. The tubular glass 59 is colorless and transparent. Light passes from the inside of the tubular glass 59 at an uncovered section (see "US" in FIG. 4), which is not attached to the hollow tube 57.

Figure 14:
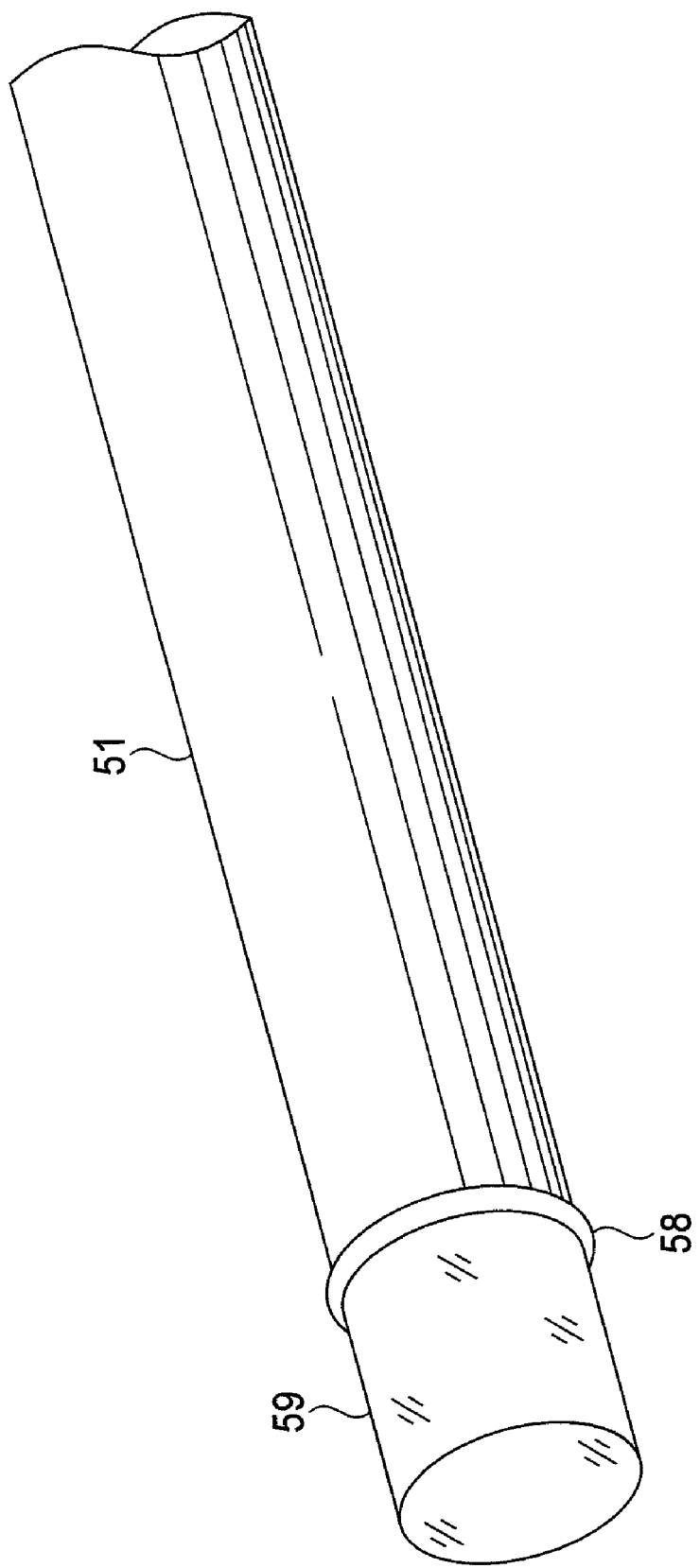
FIG. 14 is a perspective view of the distal end of the insertion tube.

As shown in FIG. 14, the first and second image fibers 55a and 55b, the hollow tube 57, the ring lens 58, and the tubular glass 59 are positioned so that the tubular glass 59 and the ring lens 58 protrude from the distal end of the insertion tube 51.

As shown in FIG. 4, a mirror fixing plate 60 is tightly adhered to the tubular glass 59 on an end of the tubular glass 59 opposite to the end attached to the hollow tube 57. By tightly adhering the mirror fixing plate 60 to the tubular glass 59, water is prevented from entering the inside of the hollow tube 57. The mirror fixing plate 60 is made of a transparent material. The white laser beam emitted from the emission end of the illumination fiber 53 passes through the mirror fixing plate without attenuation.

Figure 15:
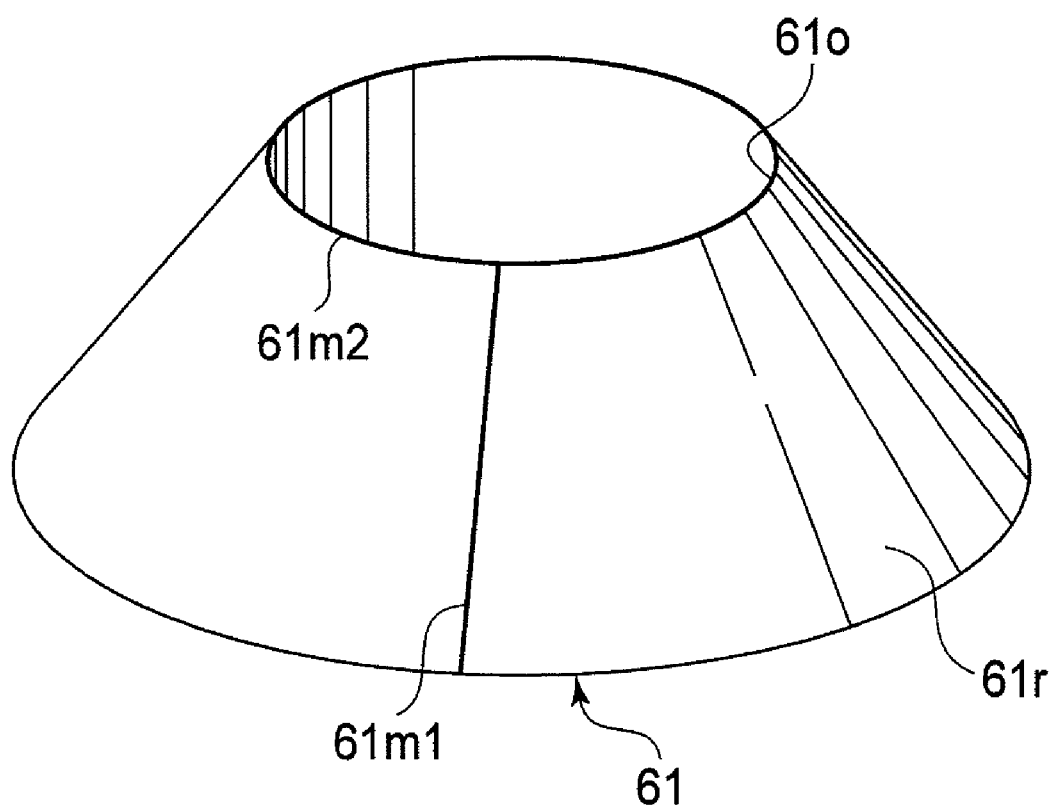
FIG. 15 is a perspective view of the mirror.

On the mirror fixing plate 60 inside of the tubular glass 59, a mirror 61 is mounted. As shown in FIG. 15, the mirror 61 is shaped as a circular truncated cone. In addition, the mirror 61 has an opening 61o at each end of the circular truncated cone.

On the side surface of the mirror 61 is a reflection surface 61r, which reflects the white laser beam emitted from the light-source unit 30. The reflection surface 61r has an initiation marker 61m1, which is a line along the generatrix line of the circular truncated cone. The initiation marker 61m1 is, for example, a black straight line, and absorbs the white laser beam incident on the initiation marker 61m1 without reflection.

The mirror 61 has a boundary marker 61m2 on the border between the side surface and the opening 61o at the small end of the circular truncated cone. The boundary marker 61m2 is a circle along the border, and the white laser beam incident on the boundary marker 61m2 is absorbed without reflection. The width of the circular boundary marker 61m2 is predetermined so that the point on the mirror 61 that is illuminated with the white laser beam emitted from the emission end, which is moved along the spiral course, crosses the boundary marker 61m2 in one rotation after first reaching the boundary marker 61m2.

The mirror 61 on the mirror fixing plate 60 is positioned so that the conical axis of the mirror 61 is aligned with a first straight line (see "L1" in FIG. 4) that passes the standard point and is parallel to the axis direction of the hollow tube 57.

Figure 16:
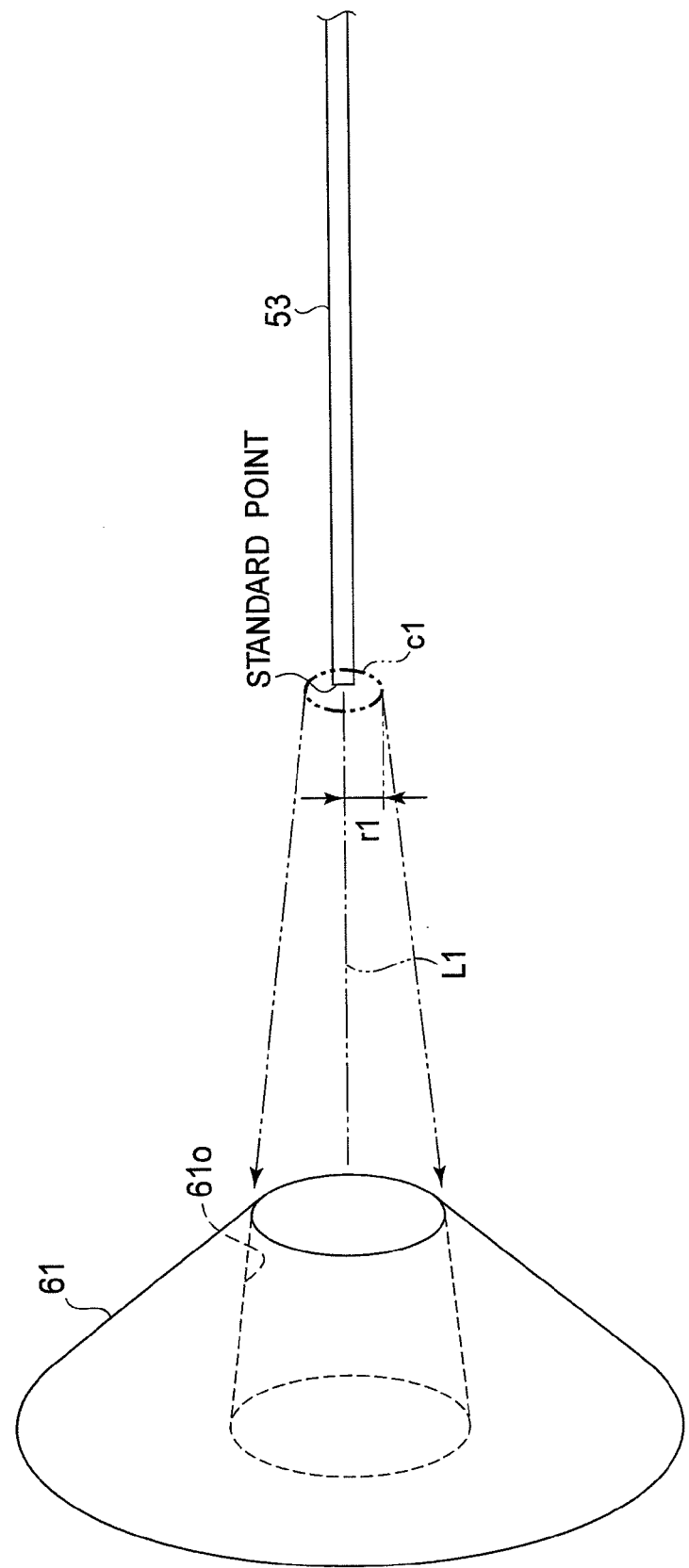
FIG. 16 is an illustration of the points on the mirror illuminated with the white laser beam when the emission end of the illumination fiber is moved along the first circumference.

As shown in FIG. 16, the opening 61o is formed by cutting along the white laser beam emitted from the emission end of the illumination fiber 53 while the emission end is moved along a first circumference (see "c1"), of which the center is in agreement with the standard point and the radius is a predetermined first radius (see "r1"). Accordingly, the inside surface of the opening 61o is parallel to the conical surface of an imaginary cone whose axis is in agreement with the first straight line (see "L1").

In addition, the mirror 61 is formed so that when the distance between the emission end of the illumination fiber 53 and the standard point is greater than the first radius, the white laser beam emitted from the emission end that strikes the reflection surface 61r will be reflected toward the uncovered section of the tubular glass 59, but will not be reflected toward the hollow tube 57.

As shown in FIG. 4, the end of the tubular glass 59 attached to the hollow tube 57 is entirely coated with a shielding film 59f (shield). The shielding film 59f prevents the white laser beam, which is partially reflected toward the tubular glass 59, from entering the incident ends of the second image fibers 55b via the ring lens 58.

Figure 17:
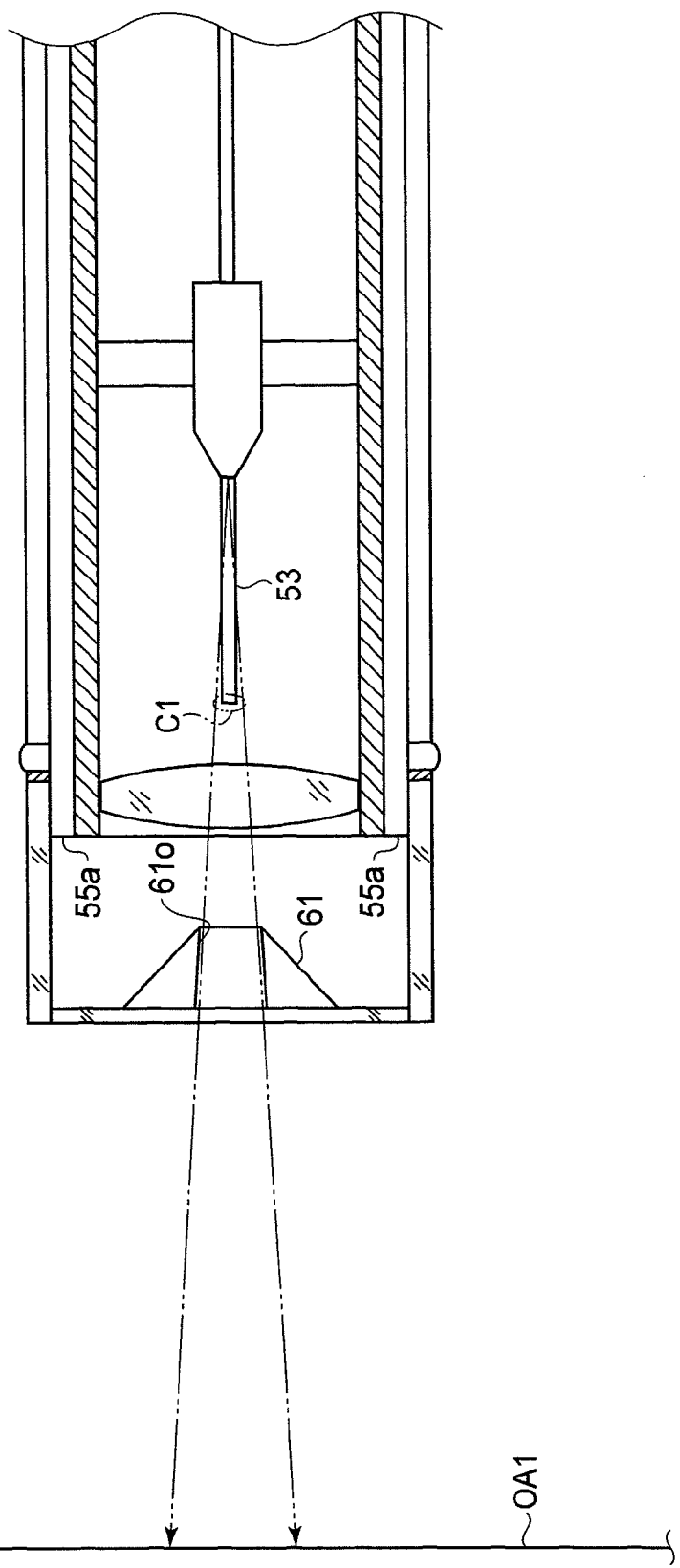
FIG. 17 is an illustration of a location illuminated with the white laser beam when it passes through the hole.

As shown in FIG. 17, since the movement of the emission end of the illumination fiber 53 begins at the standard point and continues until the emission end reaches the first circumference (see "C1"), the white laser beam emitted from the emission end passes inside of the opening 61o of the mirror 61 through the mirror fixing plate 60. And the white laser beam is shined on the first observation area (see "OA1") facing the distal end of the insertion tube 51. The point of the first observation area illuminated with the white laser beam is moved along the spiral course similar to the course along which the emission end is moved.

The reflected light is scattered at the point on the first observation area illuminated with the white laser beam. The reflected light is made incident on the incident ends of the first image fibers 55a. The reflected light incident on the incident ends of the first image fibers 55a is transmitted to the emission ends the first image fibers 55a. As described above, the emission ends of the first image fibers 55a are optically connected to the light-capturing unit 21. The reflected light transmitted to the emission ends is incident on the light-capturing unit 21.

Figure 18:
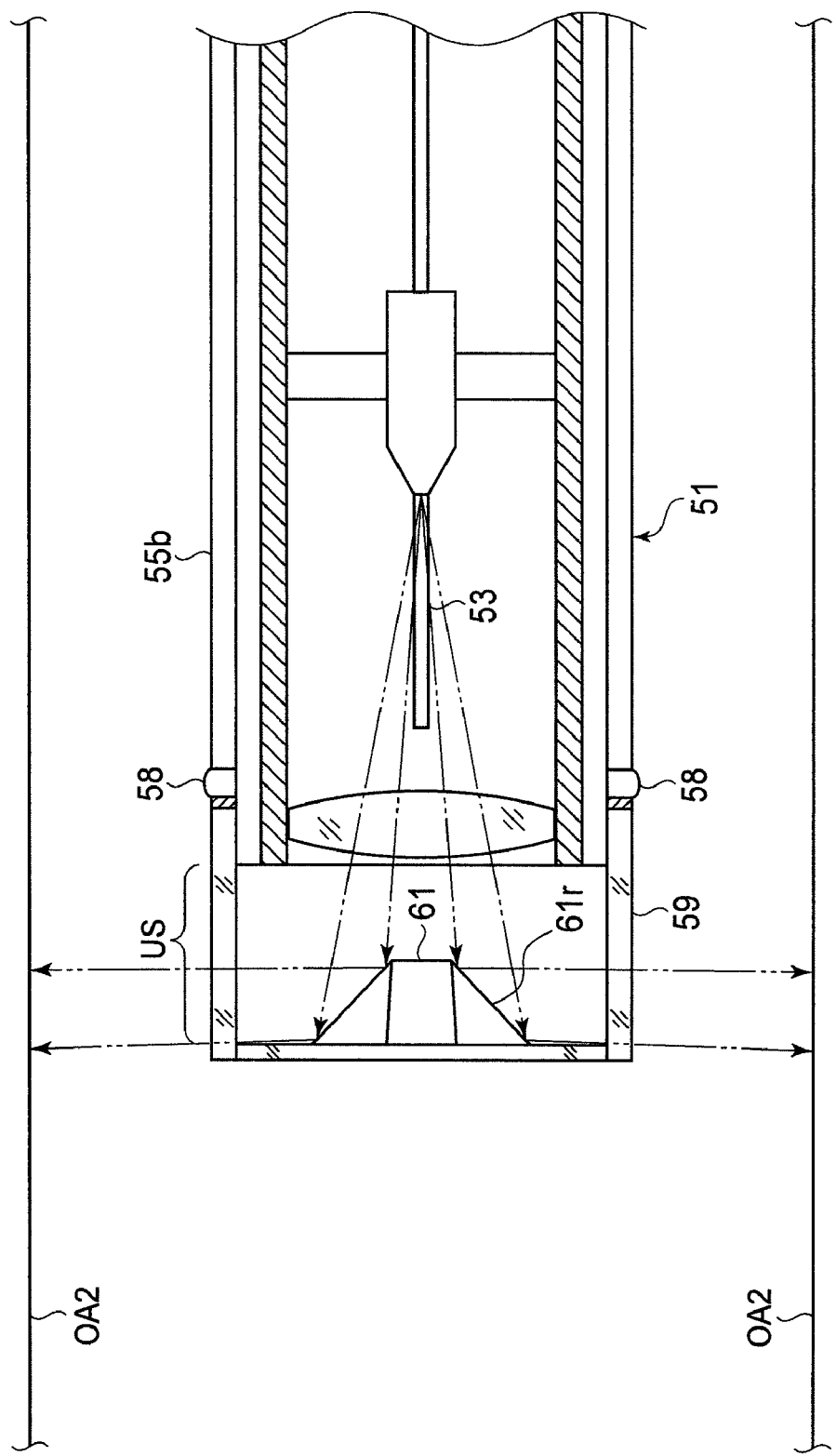
FIG. 18 is an illustration of a location illuminated with the white laser beam when it is reflected by the reflection surface.

As shown in FIG. 18, when the emission end of the illumination fiber 53 is moved outside of the first circumference, the white laser beam emitted from the emission end is reflected by the reflection surface 61r of the mirror 61, passes through the uncovered section (see "US") of the tubular glass 59, and shined on the second observation area (see "OA2") around the tubular glass 59.

Figure 19:
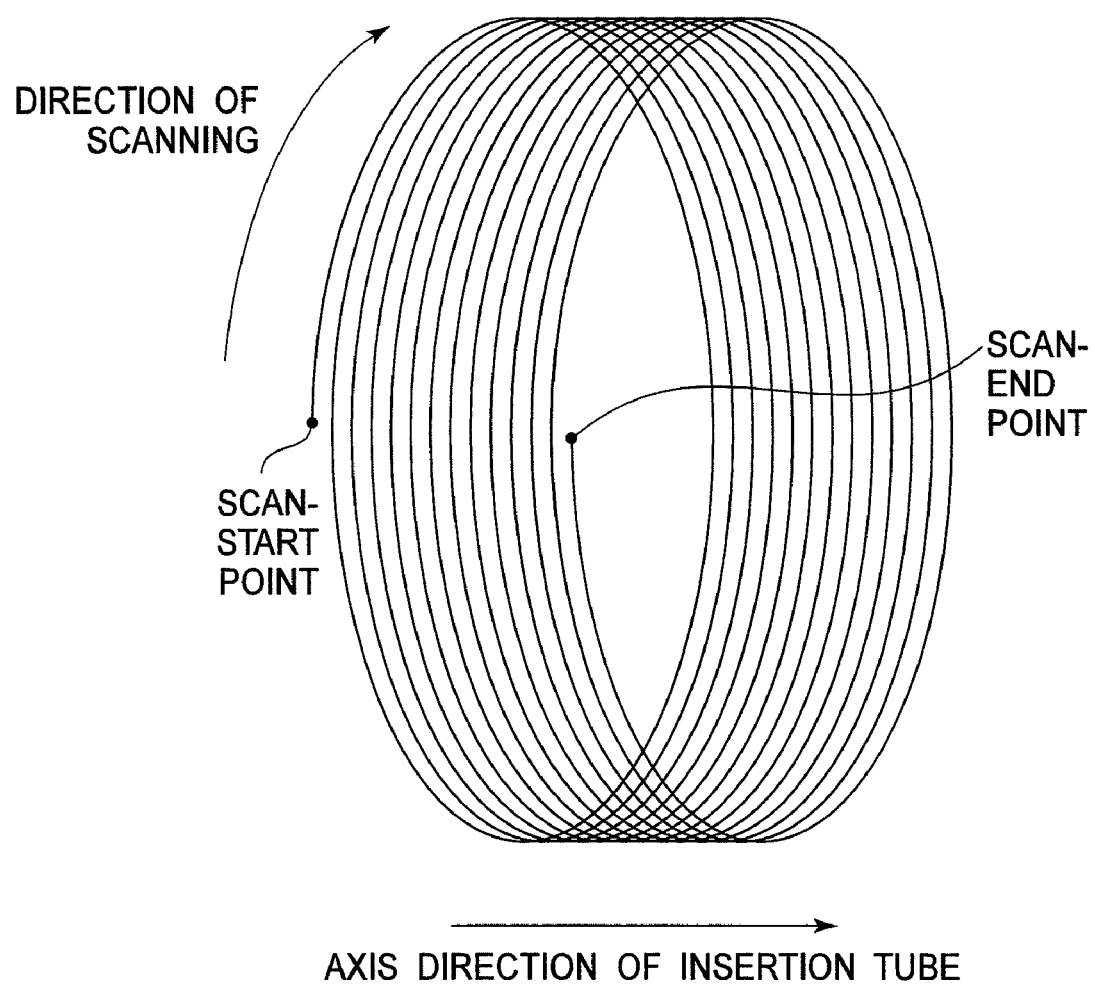
FIG. 19 is an illustration of a locus of the points of the observation area that are illuminated with the white laser beam emitted from the moving emission end of the illumination fiber.

As shown in FIG. 19, the point of the second observation area illuminated with the white laser beam, which passes through the uncovered area, moves along a helical course. The second observation area is scanned with the white laser beam by moving the illuminated point along the helical course. The point on the second observation area, which is illuminated by the white laser beam when the white laser beam emitted from the emission end reaches the intersection point of the initiation marker 61m1 and the boundary marker 61m2 is defined as scan-start point. The point of the second observation area, which is illuminated with the white laser beam when the emission end of the illumination fiber 53 is on the farthest point from the center of the spiral course, is defined as a scan-end point.

The reflected light is scattered at the point on the second observation area that is illuminated with the white laser beam. The reflected light is condensed by the ring lens 58, and is made incident on the incident ends of the second image fibers 55b (see FIG. 18). The reflected light incident on the incident ends of the second image fibers 55b is transmitted to the emission ends of the second image fibers 55b. As described above, the emission ends of the second image fibers 55b are optically connected to the light-capturing unit 21. The reflected light transmitted to the emission ends is incident on the light-capturing unit 21.

The light-capturing unit 21 detects the amounts of red, green, and blue light components in the reflected light, and generates pixel signals according to the amounts of the light components. The pixel signals are transmitted to the image processing circuit 23.

While the emission end of the illumination fiber 53 is moved along the first circumference, the frequency of generation of the pixel signals is adjusted so that the frequency is in proportion to the distance between the standard point and the position of the emission end. When the emission end of the illumination fiber 53 is moved along the spiral course at a constant angular velocity, the distance between the points on the first observation area that are illuminated with the white laser beam varies according to the distance between the points and the standard point. Accordingly, by adjusting the frequency of generation of the pixel signals in the above manner, the generation of unnecessary pixel signals near the standard point can be prevented.

The image processing circuit 23 estimates the points where the white laser beam is shined on the basis of signals used to control the scanner driver 22. In addition, the image processing circuit 23 stores the received pixel signals at the address of the image memory 26 that corresponds to the estimated points.

The image memory 26 comprises first and second storage areas. The first and second storage areas are prepared for images of the first and second observation areas, respectively. Accordingly, while the emission end of the illumination fiber 53 is moved within the first circumference, the generated pixel signals are stored in the first storage area. On the other hand, while the emission end is moved outside of the first circumference, the generated pixel signals are stored in the second storage area.

As described above, the first and second observation areas are scanned with the white laser beam, pixel signals are generated on the basis of the reflected light at the respective points illuminated with the white laser beam, and the generated pixel signals are stored at the address corresponding to the points. The image signal corresponding to the first and second observation areas comprise the pixel signals corresponding to the points from the standard point to the scan-end point. As described above, the image processing circuit 23 carries out predetermined image processing on the image signals. After undergoing predetermined image processing, the image signals are transmitted to the monitor 11.

Figure 20:
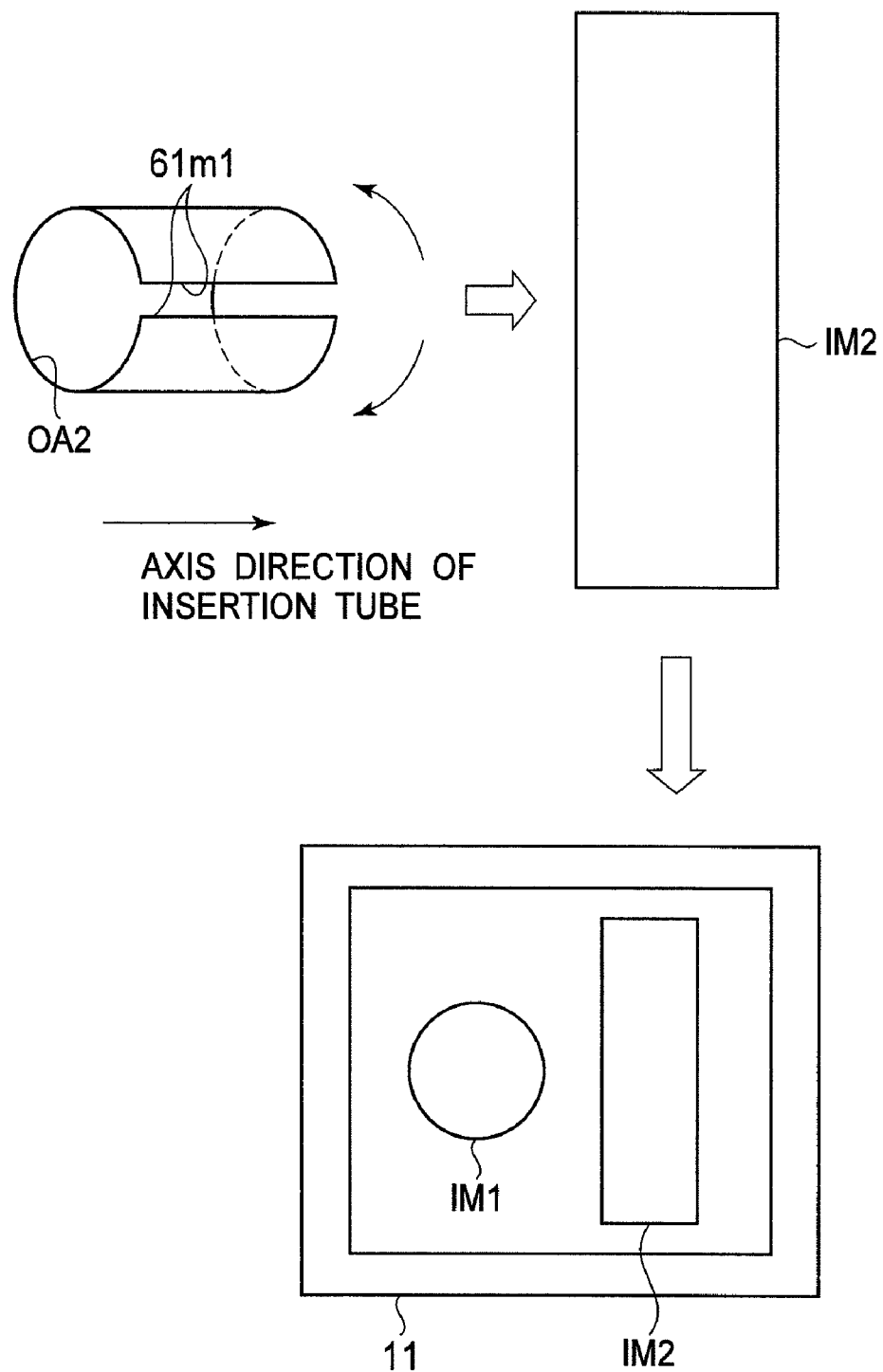
FIG. 20 is an illustration of the relationship between the form of the second observation area scanned with the white laser beam and the development chart displayed on the monitor.

As shown in FIG. 20, first and second images (see "IM1" and "IM2"; front image and side image) corresponding to the first and second observation areas, respectively, are simultaneously displayed on the monitor 11. The development chart of the second observation area (see "OA2") scanned with the white laser beam along the helical course is displayed on the monitor 11. The development chart is a chart opened along the generatrix line, which corresponds to the initiation marker 61m1, of the cylindrical image of the second observation area.

In addition to the points where the white laser beam has been shined, the position of the emission end of the illumination fiber 53 is also estimated by the image processing circuit 23 on the basis of signals used to control the scanner driver 22. In addition, as explained below, the points in time when the white laser beam is shined on the initiation marker 61m1 and the boundary marker 61m2 are used for estimating the position of the emission end of the illumination fiber 53.

Figure 21:
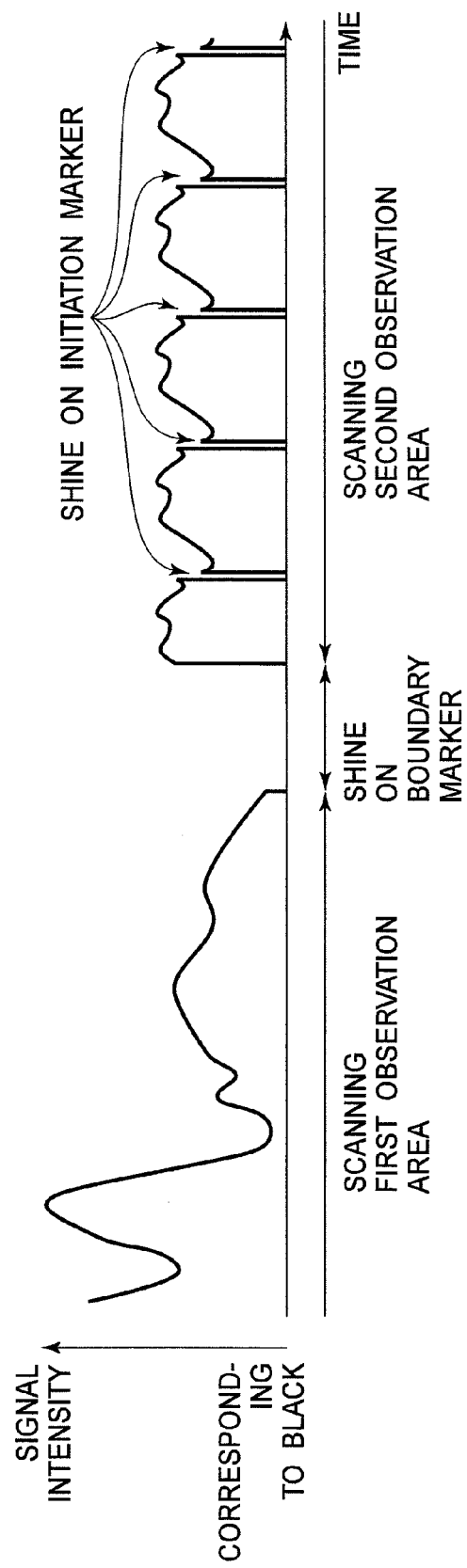
FIG. 21 is a graph illustrating the relationship between the signal intensity of the pixel signal and the elapsed time.

As described above, when the white laser beam is incident on the initiation marker 61m1 and the boundary marker 61m2, the white laser beam is absorbed and the white laser beam does not reach the first and second observation areas. Accordingly, as shown in FIG. 21, the points in time when the signal intensity of the pixel signals is lowered to the intensity corresponding to black are determined to be the instances when the point illuminated with the white laser beam is on the initiation marker 61m1 or the boundary marker 61m2.

The period during which the point on the mirror 61 illuminated with the white laser beam is moved along the boundary marker 61m2 is equal to the period in which the emission end of the illumination fiber 53 is circulated once along the spiral course, and is longer than the period required for the illuminated point to cross the initiation marker 61m1. Accordingly, it can be determined whether the illuminated point is moved on the boundary maker 61m2 or the illuminated point crosses the initiation marker 61m1 on the basis of the length of the period during which the signal intensity of the pixel signals is lowered to the signal intensity corresponding to black.

In the above embodiment, optical images of subjects in front of the distal end of the insertion tube 51 and around the periphery surrounding the insertion tube 51 can be observed. Accordingly, a front view of an internal wall of a thin lumen can be observed with an image in the direction of the distal end.

The mirror 61 is shaped as a circular truncated cone having the opening 61o that extends from the smaller end to the larger end, in the above embodiment. However, the shape of the mirror 61 is not limited to the circular truncated cone. Other shapes can be adopted as long as the distance from the first position on the first straight line and any second position on the reflection surface 61r increases with the distance between the first position and the illumination fiber 53. The line connecting the first and second positions is perpendicular to the first straight line. In other words, other shape can be adopted as long as the distance from the first position to any second position increases as the first position is moved to the first direction. For example, the shape of a bowl or a bell can be adopted.

The inside surface of the opening 61o is parallel to the conical surface of an imaginary cone whose axis is in agreement with the first straight line, in the above embodiment. However, the inside surface does not have to be parallel to the conical surface. Any shapes can be adopted for the opening 61o as long as the white laser beam emitted from the emission end of the illumination fiber 53 can bypass the mirror 61 and maintain its unaltered forward direction while the emission end is moved within the first circumference.

For example, the inside surface can be parallel to the first direction. In such a shape, the white laser beam may be shined on the inside surface of the opening 61o. However, the inside surface colored black can be used for the boundary marker 61m2. Or, a slit can be formed on the mirror 61 as the opening 61o so that the white laser beam emitted from the emission end can pass through the slit.

The opening 61o is formed on the mirror 61, in the above embodiment. However, the opening 61o need not be formed as long as the white laser beam emitted from the emission end can pass through the mirror 61 without altering the forward direction of the laser while the emission end is moved within the first circumference. For example, a colorless and transparent material can replace the opening 61o so that the white laser beam passes through the colorless and transparent material.

The scanning endoscope 50 comprises the first and second image fibers 55a and 55b for transmitting the light reflected from the first and second observation areas, respectively, in the above embodiment. However, one group of image fibers can be shared for transmitting the light reflected from the first and second observation areas. But it is preferable to mount the first and second image fibers 55a and 55b in the scanning endoscope 50 in the above embodiment in order to maximize the amount of light that is reflected from the first and second observation areas and incident on the incident end.

It is possible to estimate the position of the emission end of the illumination fiber 53 without the pixel signals corresponding to the initiation marker 61m1 and the boundary marker 61m2. However, by estimating the position of the emission end using not only signals to control the scanner driver, but also the time required for the white laser beam to cross the initiation marker 61m1 and move along the boundary marker 61m2, as in the above embodiment, the accuracy of the estimation can be improved.

The end of the tubular glass 59 is entirely coated with a shielding film 59f, in the above embodiment. However, the end of the tubular glass 59 does not need to be coated with the shielding film 59f. It is possible to make only the reflected light from the second observation area incident on the incident ends of the second image fibers 55b without the shielding film 59f. However, to produce a more accurate image it is preferable to prevent the white laser beam reflected by the mirror 61 from entering the incident end of the second image fibers 55b. Accordingly, it is preferable to coat the end of the tubular glass 59 with the shielding film 59f, as in the above embodiment.

The emission end of the illumination fiber 53 is moved along the spiral course, in the above embodiment. However, the first and second observation areas can be scanned with the white laser beam even if the emission end is moved along other courses.

The white laser beam is emitted from the light-source unit 30, as in the embodiment. The light-source unit 30 may emit other kinds of light, such as excitation light which excites an organ to fluoresce. Then, autofluorescence incident on the incident end of the first and second image fibers 55a and 55b can be transmitted to the light-capturing unit 21, and the image can be produced on the basis of the autofluorescence.

The points in time for generating the pixel signals are adjusted so that the frequency of generation of the pixel signals is in proportion to the distance between the standard point and the location of the emission end of the illumination fiber 53 while the white laser beam is shined on the first observation area, in the above embodiment. But the points in time for generating the pixel signals need not be adjusted. However, as described above, it is preferable to adjust the points in time for generating the pixel signals in order to prevent unnecessary pixel signals from being generated.

Although the embodiments of the present invention have been described herein with reference to the accompanying drawings, obviously many modifications and changes may be made by those skilled in this art without departing from the scope of the invention.

The present disclosure relates to subject matter contained in Japanese Patent Application No. 2008-296143 (filed on Nov. 19, 2008), which is expressly incorporated herein, by reference, in its entirety.

The invention claimed is:

1. A scanning endoscope comprising:
a first transmitter that has a first emission end, the first transmitter emitting a beam of radiant light from the first emission end, the beam of the radiant light being shined on an observation area;
an actuator that moves the first emission end in a direction perpendicular to an emission direction, the beam of the radiant light being emitted from the first emission end of the first transmitter in the emission direction; and
a mirror that is arranged from the first emission end to the first direction, the first direction being the emission direction when the emission end is on a standard point, the mirror comprising a through-part and a reflection surface, the radiant light emitted from the first emission end passing through the through-part when the first emission end is within a first circumference, a center of the first circumference being in agreement with the standard point, the radius of the first circumference being a first length, the reflection surface being formed around a first straight line, the first straight line being parallel to the first direction and including the standard point, the distance between a first position on the first straight line and any second position on the reflection surface increasing as the first position is moved in the first direction, the reflection surface reflecting the radiant light emitted from the first emission end toward the observation area around the first straight line when the first emission end is outside of the first circumference, a line connecting the first and second positions being perpendicular to the first straight line.

2. A scanning endoscope according to claim 1, further comprising:
a second transmitter that has a second incident end and a second emission end, the second transmitter being arranged so that the second incident end faces toward the first direction, reflected light or fluorescence at the observation area, which is illuminated with the radiant light that passes through the through-part, being made incident on the second incident end, the second transmitter transmitting the reflected light or the fluorescence incident on the second incident end to the second emission end;
a third transmitter that has a third incident end and a third emission end, reflected light or fluorescence at the observation area, which is illuminated with the radiant light that is reflected by the reflection surface, being made incident on the third incident end, the third transmitter transmitting the reflected light or the fluorescence incident on the third incident end to the third emission end;
a shield that prevents the radiant light that is reflected by the reflection surface and reaches the third incident end without reaching the observation area from entering the third incident end.

3. A scanning endoscope according to claim 1, wherein the through-part is an opening.

4. A scanning endoscope according to claim 3, wherein,
the actuator moves the first emission end by bending the first transmitter near the emission end,
the inside surface of the opening is a conical surface of a circular truncated cone, of which a generatrix line is in agreement with a straight line from the first emission end in the emission direction when the first emission end is on the first circumference.

5. A scanning endoscope according to claim 3, wherein the inside surface of the opening is in agreement with a side surface of a cylinder of which the axis is parallel to the first direction, the inside surface having a shield which absorbs the radiant light.

6. A scanning endoscope according to claim 1, further comprising a first marker at the boundary between the through-part and the reflection surface, the first marker absorbing the radiant light.

7. A scanning endoscope according to claim 1, wherein the reflection surface is parallel to a circular truncated cone of which the axis is in agreement with the first straight line.

8. A scanning endoscope according to claim 7, further comprising a second marker that absorbs the radiant light, the second marker being a straight line parallel to a generatrix line of the circular truncated cone of the reflection surface.

9. A scanning endoscope according to claim 1, wherein the actuator moves the first emission end along a spiral course of which the center is in agreement with the standard point.

10. A scanning endoscope processor comprising:
a light source that supplies the radiant light that is emitted from the first emission end to the first transmitter of the scanning endoscope of claim 1;
a light receiver that receives and detects the amount of reflected light or fluorescence at the observation area illuminated with the radiant light;
an image processor that produces an image corresponding to the observation area on the basis of the amount of the reflected light or the fluorescence detected by the light receiver; and
a controller that orders the image processor to generate a front image when the first emission end is moved within the first circumference, the controller ordering the image processor to generate a side image when the first emission end is moved outside of the first circumference, the front image being an image of the observation area in the first direction from the first emission end, the side image being an image of the observation area around the first straight line near the first emission end.

11. A scanning endoscope apparatus comprising the scanning endoscope according to claim 1 and the scanning endoscope processor comprising:
a light source that supplies the radiant light that is emitted from the first emission end to the first transmitter of the scanning endoscope of claim 1;
a light receiver that receives and detects the amount of reflected light or fluorescence at the observation area illuminated with the radiant light;
an image processor that produces an image corresponding to the observation area on the basis of the amount of the reflected light or the fluorescence detected by the light receiver; and
a controller that orders the image processor to generate a front image when the first emission end is moved within the first circumference, the controller ordering the image processor to generate a side image when the first emission end is moved outside of the first circumference, the front image being an image of the observation area in the first direction from the first emission end, the side image being an image of the observation area around the first straight line near the first emission end.

* * * * *